US011918570B2

(12) United States Patent
Pisconti et al.

(10) Patent No.: US 11,918,570 B2
(45) Date of Patent: Mar. 5, 2024

(54) METHOD OF TREATMENT FOR PREVENTION OF GLUCOCORTICOID TOXICITY AND/OR ENHANCEMENT OF MUSCLE REGENERATION VIA NEUTROPHIL ELASTASE INHIBITION

(71) Applicants: The Research Foundation for The State University of New York, Albany, NY (US); The University of Liverpool, Liverpool (GB)

(72) Inventors: Addolorata Pisconti, Port Jefferson, NY (US); Fiona Kate Jones, East Setauket, NY (US); Kirsty Anne Johnson, Wirral (GB)

(73) Assignees: The Research Foundation for The State University of New York, Albany, NY (US); The University of Liverpool, Liverpool (GB)

( * ) Notice: Subject to any disclaimer, the term of this patent is extended or adjusted under 35 U.S.C. 154(b) by 0 days.

(21) Appl. No.: 17/228,931

(22) Filed: Apr. 13, 2021

(65) Prior Publication Data
US 2021/0315873 A1    Oct. 14, 2021

Related U.S. Application Data

(60) Provisional application No. 63/009,038, filed on Apr. 13, 2020.

(51) Int. Cl.
*A61K 31/444* (2006.01)
*A61K 31/573* (2006.01)
*A61P 21/00* (2006.01)

(52) U.S. Cl.
CPC .......... *A61K 31/444* (2013.01); *A61K 31/573* (2013.01); *A61P 21/00* (2018.01)

(58) Field of Classification Search
CPC ...... A61K 45/06; A61K 38/005; A61K 31/00; A61K 31/444; A61K 31/573
USPC ......................................................... 514/172
See application file for complete search history.

(56) References Cited

U.S. PATENT DOCUMENTS

| | | | |
|---|---|---|---|
| 8,404,268 | B2 | 3/2013 | Lee et al. |
| 9,669,026 | B2 | 6/2017 | May |
| 10,231,976 | B2 | 3/2019 | Du |
| 10,874,652 | B2 | 12/2020 | Pisconti |
| 2008/0146585 | A1 | 6/2008 | Moussy et al. |
| 2013/0045179 | A1 | 2/2013 | Ciustea et al. |
| 2015/0152048 | A1 | 6/2015 | Imagawa et al. |
| 2016/0101072 | A1 | 4/2016 | Mulvany et al. |
| 2019/0134014 | A1* | 5/2019 | Pisconti ............... A61K 38/005 |
| 2019/0134914 | A1* | 5/2019 | Gonzalez ................ G06F 30/20 |
| 2021/0015807 | A1* | 1/2021 | Poydenot ................ A61P 21/00 |
| 2021/0196694 | A1* | 7/2021 | Pisconti .................. A61P 21/00 |

FOREIGN PATENT DOCUMENTS

| | | |
|---|---|---|
| CN | 111867632 A | 10/2020 |
| CN | 111989098 A | 11/2020 |
| JP | 2007500243 A | 1/2007 |
| JP | 2011519961 A | 7/2011 |
| JP | 2016539927 A | 12/2016 |
| JP | 2019504064 A | 2/2019 |
| JP | 6502876 B2 | 4/2019 |
| JP | 2020500197 A | 1/2020 |
| JP | 2020536057 A | 12/2020 |
| JP | 2020536058 A | 12/2020 |
| JP | 2020536060 A | 12/2020 |
| JP | 2021063107 A | 4/2021 |
| JP | 2023532972 A | 8/2023 |
| KR | 20120013404 A | 2/2012 |
| KR | 20160059241 A | 5/2016 |
| KR | 20160069802 A | 6/2016 |

OTHER PUBLICATIONS

Smith LR, Barton ER. SMASH—semi-automatic muscle analysis using segmentation of histology: a MATLAB application. Skelet Muscle. Nov. 27, 2014;4:21. doi: 10.1186/2044-5040-4-21. PMID: 25937889; PMCID: PMC4417508.*
Ramamoorthy et al., Corticosteroids-Mechanisms of Action in Health and Disease, Rheum Dis Clin North Am. Feb. 2016 ; 42(1): 15-31.*
Webster et al., Inflammation and Skeletal Muscle Wasting During Cachexia, Front. Physiol., Nov. 19, 2020, Article 597675, pp. 1-22 ("Webster").*
Mah, Current and emerging treatment strategies for Cuchenne muscular dystrophy, Neuropsychiatric Disease and Treatment 2016: 12 1795-1807.*
Arecco N. et al., "Elastase Levels and Activity are Increased in Dystrophic Muscle and Impair Myoblast Cell Survival, Proliferation and Differentiation", Scientific Reports 6(1):1-20 (May 31, 2016).
Henriksen P.A., "The Potential of Neutrophil Elastase Inhibitors as Anti-Inflammatory Therapies", Current Opinion in Hamatology 21(1):23-28 (Jan. 2014).
Kharraz Y. et al., "Understanding the Process of Fibrosis in Duchenne Muscular Dystrophy", BioMed Research International 2014(ID965631):1-11 (Jan. 8, 2014).
Mah J K, "Current and Emerging Treatment Strategies for Duchenne Muscular Dystrophy", Neuropsychiatric Disease and Treatment 2016(12):1795-1807 (May 10, 2016).
Nussbaum F V et al., "Neutrophil Elastase Inhibitors for the Treatment of (Cardio) Pulmonary Diseases: Into Clinical Testing With Pre-Adaptive Pharmacophores", Bioorganic & Medicinal Chemistry Letters 25:4370-4381 (Aug. 20, 2015).

(Continued)

*Primary Examiner* — Svetlana M Ivanova
(74) *Attorney, Agent, or Firm* — Scully, Scott, Murphy & Presser, P.C.

(57) ABSTRACT

The present disclosure is directed to methods of treatment, including treatment of a myopathy by administering to a subject in need thereof an elastase inhibitor in combination with a glucocorticoid. The present disclosure is also directed to pharmaceutical compositions that include an elastase inhibitor that can be used in such treatment.

13 Claims, 21 Drawing Sheets
(11 of 21 Drawing Sheet(s) Filed in Color)

(56) References Cited

OTHER PUBLICATIONS

International Search Report dated Aug. 2, 2017 received in International Application No. PCT/GB2017/051349.
Stockley R. et al., "Phase II Study of a Neutrophil Elastase Inhibitor (AZD9668) in Patients With Bronchiectasis", Respiratory Medicine 107:524-533 (2013).
U.S. non-Final Office Action dated Aug. 1, 2022 received in related U.S. Appl. No. 17/104,192.

* cited by examiner

Plcb vs Pred: p = n.s.
Plcb vs A10+P: p<0.05 after day 6, p<0.01 after day 11
Pred vs A10+P: p<0.05 after day 3, p<0.01 after day 6

METHOD OF TREATMENT FOR PREVENTION OF GLUCOCORTICOID TOXICITY AND/OR ENHANCEMENT OF MUSCLE REGENERATION VIA NEUTROPHIL ELASTASE INHIBITION

CROSS REFERENCE TO RELATED APPLICATIONS

The present application claims the benefit of priority from U.S. Provisional Application No. 63/009,038, filed on Apr. 13, 2020, the content of which is incorporated herein by reference in its entirety.

FIELD OF THE DISCLOSURE

The present disclosure relates to elastase inhibitors in combination with a glucocorticoid for use in the promotion of muscle regeneration, prevention of steroid-induced muscle atrophy and enhancement of anti-inflammatory activity in the treatment of a myopathy. The disclosure also relates to methods of promoting muscle regeneration prevention of steroid-induced muscle atrophy and enhancement of anti-inflammatory activity in the treatment of a myopathy, as well as pharmaceutical compositions comprising an elastase inhibitor in combination with a glucocorticoid for use in the promotion of muscle regeneration in the treatment of a myopathy.

BACKGROUND

Glucocorticoids are steroidal hormones involved in the regulation of glucose metabolism (hence the name) and many other biological processes including inflammation. Glucocorticoids and their derivatives (such as prednisolone, dexamethasone, hydrocortisone, etc.) are widely used in clinical practice to treat a plethora of inflammatory conditions, from autoimmune disorders (e.g. rheumatoid arthritis) to allergic, infectious and genetic disorders. Although the anti-inflammatory activity of glucocorticoids is significant and leads to beneficial outcomes in most patients, their prolonged use is not advised due to a series of serious side effects such as: insulin intolerance, muscle atrophy (which then further worsens insulin resistance), mood disorders, loss of bone density and complications at the level of various organs.

Duchenne Muscular Dystrophy (DMD) is a genetic disorder affecting muscle cells that leads to chronic inflammation in the muscle, loss of muscle mass and strength and premature death. Though a number of gene therapy strategies to tackle DMD are in clinical trial, there is currently no cure for DMD. The current standard of care for DMD is based on glucocorticoids. Although glucocorticoids appear relatively beneficial in the first years of the disease, children and teenagers affected by DMD are often forced to abandon their glucocorticoid-based therapy, when the side effects become unbearable.

To date there is no cure or effective treatment for Duchenne muscular dystrophy. The management is currently based on the use of glucocorticoids, which delay loss of ambulation and cardiomyopathy but also cause significant side effects often poorly tolerated by children and teenagers with Duchenne muscular dystrophy.

It is an aim of certain embodiments of the disclosure to obviate or mitigate at least some of the problems noted above. It is an aim of certain embodiments of the disclosure to provide agents for use in the promotion of muscle regeneration prevention of steroid-induced muscle atrophy and enhancement of anti-inflammatory activity in the treatment of myopathies, such as muscular dystrophy. It is an aim of certain embodiments of the disclosure to provide methods of treatment for use in the promotion of muscle regeneration prevention of steroid-induced muscle atrophy and enhancement of anti-inflammatory activity in the treatment of myopathies, such as muscular dystrophy. It is an aim of certain embodiments of the disclosure to provide pharmaceutical compositions for use in the promotion of muscle regeneration in the treatment of myopathies, such as muscular dystrophy.

SUMMARY OF THE DISCLOSURE

The present disclosure is directed to methods of treatment, including treatment of myopathy by administering to a subject in need thereof an elastase inhibitor in combination with a glucocorticoid. The present disclosure is also directed to pharmaceutical compositions that includes an elastase inhibitor that can be used in such treatment.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

The present disclosure will be better understood by reference to the following drawings, which are provided as illustrative of certain embodiments of the subject application, and not meant to limit the scope of the present disclosure.

DETAILED DESCRIPTION OF EMBODIMENTS OF THE DISCLOSURE

Figures 1A, 1B, 1C, 1D, 1E:
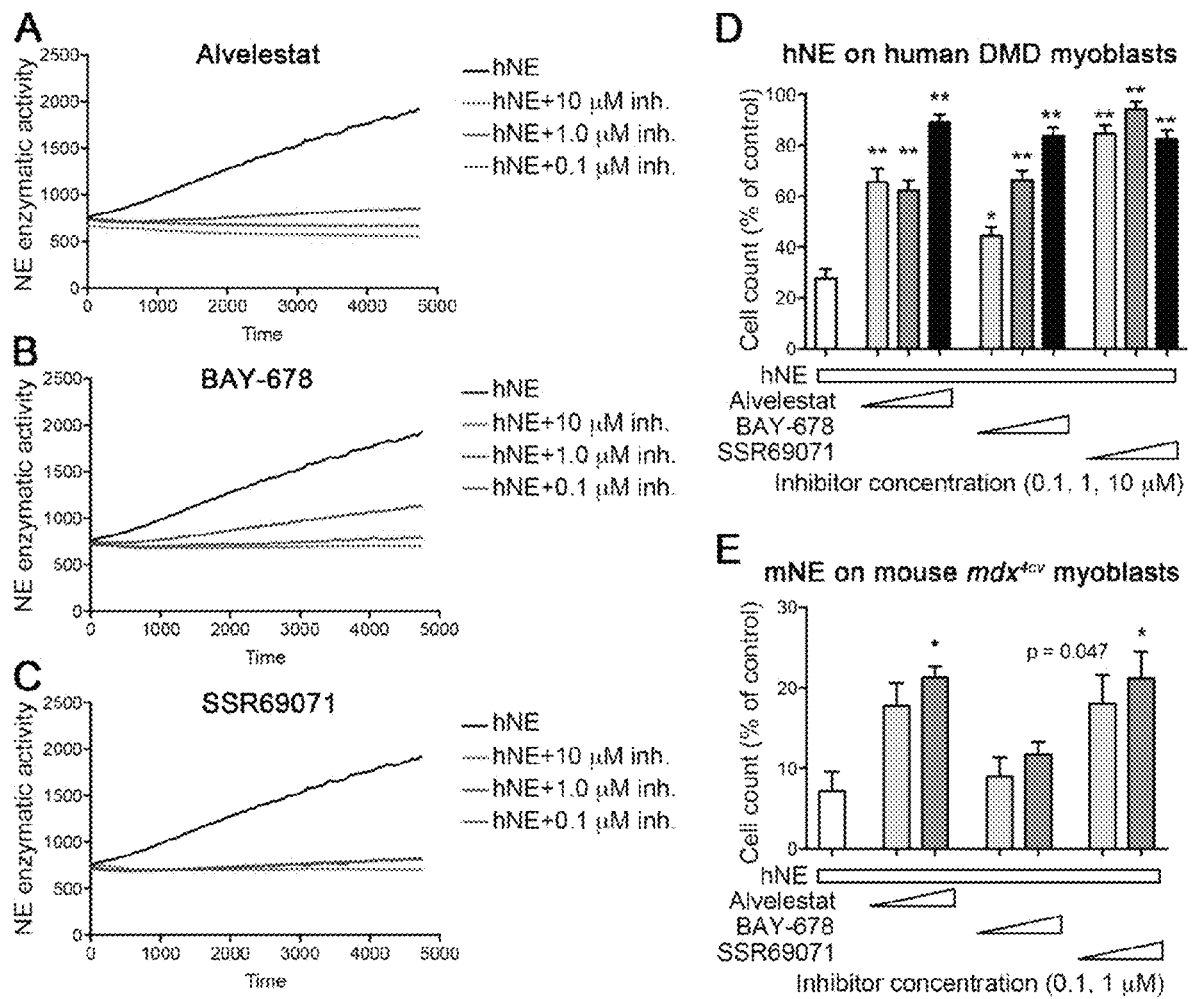
FIGS. 1A-1E illustrate that three selective neutrophil elastase (NE) inhibitors (Alvelestat, BAY-678 and SSR69071) are similarly potent at inhibiting human NE activity in vitro (FIGS. 1A-1C) and similarly effective at rescuing NE-induced myoblast cell death ex vivo (FIGS. 1C and 1D).

The following detailed description of embodiments of the disclosure will be made in reference to the accompanying drawings. In describing the disclosure, explanation about related functions or constructions known in the art are omitted for the sake of clearness in understanding the concept of the disclosure to avoid obscuring the disclosure with unnecessary detail.

In the discussion and claims herein, the term "about" indicates that the value listed may be somewhat altered, as long as the alteration does not result in nonconformance of the process or device. For example, for some elements the term "about" can refer to a variation of ±0.1%, for other elements, the term "about" can refer to a variation of ±1% or ±10%, or any point therein.

As used herein, the term "substantially", or "substantial", is equally applicable when used in a negative connotation to refer to the complete or near complete lack of an action, characteristic, property, state, structure, item, or result. For example, a surface that is "substantially" flat would be either completely flat, or so nearly flat that the effect would be the same as if it were completely flat.

As used herein terms such as "a", "an" and "the" are not intended to refer to only a singular entity, but include the general class of which a specific example may be used for illustration.

As used herein, terms defined in the singular are intended to include those terms defined in the plural and vice versa.

References in the specification to "one aspect", "certain aspects", "some aspects" or "an aspect", indicate that the aspect(s) described may include a particular feature or characteristic, but every aspect may not necessarily include the particular feature, structure, or characteristic. Moreover, such phrases are not necessarily referring to the same aspect. Further, when a particular feature, structure, or characteristic is described in connection with an aspect, it is submitted that it is within the knowledge of one skilled in the art to affect such feature, structure, or characteristic in connection with other aspects whether or not explicitly described. For purposes of the description hereinafter, the terms "upper", "lower", "right", "left", "vertical", "horizontal", "top", "bottom", and derivatives thereof shall relate to a scanner relative to a floor and as it is oriented in the figures.

Reference herein to any numerical range expressly includes each numerical value (including fractional numbers and whole numbers) encompassed by that range. To illustrate, reference herein to a range of "at least 50" or "at least about 50" includes whole numbers of 50, 51, 52, 53, 54, 55, 56, 57, 58, 59, 60, etc., and fractional numbers 50.1, 50.2, 50.3, 50.4, 50.5, 50.6, 50.7, 50.8, 50.9, etc. In a further illustration, reference herein to a range of "less than 50" or "less than about 50" includes whole numbers 49, 48, 47, 46, 45, 44, 43, 42, 41, 40, etc., and fractional numbers 49.9, 49.8, 49.7, 49.6, 49.5, 49.4, 49.3, 49.2, 49.1, 49.0, etc.

The inventors have surprisingly found that increased elastase levels, and especially increased neutrophil elastase levels, may impair muscle regeneration. Without wishing to be bound by any particular hypothesis, the inventors believe that increased elastase levels damage the extracellular matrix which may result in a loss of muscle progenitor cell (such as such as satellite cell, pericyte, myoendothelial cell, side population cell, mesenchymal stem cell or myoblast cell) regenerative potential.

The loss of muscle progenitor cell regenerative potential impairs the capacity of muscle tissue to regenerate. The loss of muscle progenitor cell regenerative potential may be therefore associated with the progressive loss of muscle strength and muscle mass typically observed in patients diagnosed with a myopathy, in particular muscle dystrophy such as Duchenne muscle dystrophy.

The inventors have unexpectedly found that elastase inhibitors have a protective effect on muscle progenitor cells and their regenerative potential, which aids muscle cell regeneration. This surprising finding gives rise to a new approach to the treatment of muscular dystrophies and other myopathies, which is further shown in FIGS. 1A-1E.

In FIGS. 1A-1C Human NE (hNE) was incubated for the indicated amount of time (X-axis) either alone (Control, black line) or in the presence of various concentration of inhibitor, as indicated in each graph (colored lines). The cumulative elastase activity detected over time is plotted.

In FIGS. 1D and 1E, myoblasts isolated from a patient affected by Duchenne muscular dystrophy (DMD, FIG. 1D) or from a mouse model of Duchenne muscular dystrophy (mdx$^{4cv}$, FIG. 1E) where cultured and either untreated (Control) or treated with human NE (hNE, FIG. 1D) or mouse NE (mNE, FIG. 1E), either alone or in the presence of the indicated concentration of NE inhibitors Alvelestat, BAY-678 and SSR69071. The number of live cells in each condition was counted and plotted as percentage of the number of live cells in the untreated (Control) condition. All three inhibitors are similarly effective at blocking NE-induced myoblast death, and are all most effective against human NE, which is consistent with the fact that all three inhibitors were developed to selectively inhibit human NE.

In the context of the present disclosure, the term "elastase inhibitor" refers to any compound capable of reducing elastase enzyme activity, and thereby promoting muscle regeneration. Elastases are proteases which cleave the extracellular protein elastin and other extracellular proteins such as laminins, collagens and fibronectin, as well as growth factors and their receptors and cytokines and their receptors. Accordingly, the term "elastase inhibitor" encompasses any compound capable of reducing the ability of an elastase enzyme to cleave its protein substrate.

Several methods for measuring elastase enzymatic activity are known in the art. Merely by way of example, elastase activity can be determined by measuring the fluorescence emitted by a fluorigenic peptide such as MeOSuc-Ala-Ala-Pro-Val-AFC or Suc-Ala-Ala-Ala-AMC. Fluorescence may be measured, for example, using a plate reader. Other suitable assays for measuring elastase activity will be known to the skilled person. These may include measuring the product generated by incubation with a fluorescently labelled peptide such as 5-FAM-Arg-Glu-Ala-Val-Val-Tyr or 5-FAM-Ala-Ala-Ala-Phe-Tyr-Asp using an instrument that detects the size of the fluorescently labelled probe.

According to embodiments further described herein, a class of drugs has been identified that enhances prednisolone efficacy and reduces its toxicity. In the context of muscular dystrophy, which is the disease model we have studied so far, our observations may be relevant not only to the current standard of care for muscular dystrophy, which is entirely based on glucocorticoids, but also to the various gene therapies currently in clinical trial, which still need to be combined with powerful anti-inflammatory drugs and benefit from enhancement of muscle regeneration.

In a mouse model of muscular dystrophy, the mdx4cv mouse, we have recently observed that inhibition of neutrophil elastase (via oral administration of AZD9668, a.k.a. Alvelestat or MPH-966) concomitantly with prednisolone (also orally administered, at a dose comparable to that normally prescribed to patients affected by muscular dystrophy), enhances prednisolone efficacy and reduces prednisolone induced muscle atrophy.

In a suitable embodiment, an elastase inhibitor may reduce elastase enzyme activity by at least 30%, at least 40%, at least 50%, at least 60%, or at least 70%, or more compared to normal elastase enzyme activity. Suitably, an elastase inhibitor may reduce elastase enzyme activity by at least 75%, at least 80%, at least 85%, at least 90%, at least 95% or more compared to normal elastase enzyme activity. Normal elastase enzymatic activity refers to the activity of an elastase enzyme without the presence of an elastase inhibitor.

A suitable elastase enzyme inhibitor may reduce the activity of an elastase enzyme either ex vivo or in vivo.

In a suitable embodiment term "elastase inhibitor" encompasses any compound capable of reducing the activity of one or more elastase enzymes selected from the group consisting of: neutrophil elastase, macrophage metalloelastase, chymotrypsin-like elastase family, member 1; chymotrypsin-like elastase family, member 2A; chymotrypsin-like elastase family, member 2B; chymotrypsin-like elastase family, member 3A; chymotrypsin-like elastase family, member 3B; and chymotrypsin C (caldecrin).

Alternatively, a suitable elastase enzyme inhibitor may specifically inhibit the activity of neutrophil elastase enzyme. The neutrophil elastase enzyme is the enzyme encoded by the gene ELANE.

In a suitable embodiment the elastase inhibitor is an extracellular elastase inhibitor. In a particularly suitable embodiment the extracellular elastase inhibitor is an extracellular inhibitor of neutrophil elastase.

An extracellular elastase inhibitor is any compound capable of reducing the activity of an elastase enzyme occurring outside the cell. Such elastase inhibitors may prevent the degradation of the extracellular matrix caused by increased levels and/or increased activity of extracellular elastase enzymes.

Suitably, an elastase inhibitor may be provided extracellularly at a site of a myopathy. In this context, an extracellular elastase inhibitor may be one that is unable to cross the cell membrane, and thereby enter a cell. It will be appreciated that extracellular inhibitors of elastase activity of this sort will not inhibit intracellular elastase activity if provided extracellularly at a site of a myopathy requiring treatment (for example, if provided systemically).

A suitable elastase inhibitor may be selected from the group consisting of: Alvelestat, Elastatinal, sivelestat, dociparstat, lonodelestat, tiprelestat, depelestat, lodelaben, telmesteine, BAY85-8501, BAY-678, Freselestat, AZD9819, GW-31 1616A, POL6014, SSR 69071, GW475151, ICI 200,880 and AX-9657, Midesteine, 1-(3-methylbenzoyl)-1H-indazole-3-carbonitrile, Elastase inhibitor II, Elastase inhibitor III, Elastase inhibitor V, N-(Methoxysuccinyl)-Ala-Ala-Pro-Val-chloromethyl ketone, 1,4-diarylpyrimidopyridazinyldione or a derivative thereof, 2-pyrazinone or a derivative thereof, 2-pyridone or a derivative thereof, pyridyl-3-yl-benzo[d][1,3]oxazin-4-one or a derivative thereof, 3,4,6,7-tetrahydro-1H-pyrrolo[3,4-d]pyrimidine-2, 5-dione or derivative thereof, 4-(4-Cyano-2-thioaryl)-dihydropyrimidone or a derivative thereof, 4-(4-cyanophenyl)-1-(3-trifluoromethylphenyl)-3,4,6,7-tetrahydro-1H-pyrrolo [3,4-d]pyrimidine-2,5-dione or a derivative thereof, Azetidine-2, 4-dione or a derivative thereof, Benzoxazinone or a derivative thereof, Dihydropyrimidone or a derivative thereof, functionalized N-amino-4-imidazolidinone, N-Benzoyl pyrazole or a derivative thereof, Tetrazolopyrimidine or a derivative thereof, Serpinbl, Elafin, Alpha-1-antitrypsin, Protein AMB P, Antileukoproteinase, Eppin and Alpha-2-macroglobulin.

More suitably, the elastase inhibitor may be selected from the group consisting of: Alvelestat, Elastatinal, sivelestat, dociparstat, lonodelestat, tiprelestat, depelestat, lodelaben, telmesteine, BAY85-8501, BAY-678, Freselestat and AZD9819.

A suitable elastase inhibitor may be exogenous or endogenous.

For the purpose of the present disclosure, an exogenous elastase inhibitor is one which is not naturally occurring in humans. Merely by way of example, an exogenous elastase inhibitor may be a synthetic small molecule, or an elastase inhibitor which is naturally found in bacteria (or other non-human organisms). An example of an elastase inhibitor which is naturally found in bacteria is Elastatinal.

For the purpose of the present disclosure, an endogenous elastase inhibitor is one which is naturally occurring in humans. However, it will be appreciated that an endogenous elastase inhibitor may be synthetically produced. Such a synthetically produced endogenous elastase inhibitor is one which has the same chemical structure as any elastase inhibitor that naturally occurs in humans.

Endogenous elastase inhibitors may be provided to the subject either directly or indirectly. Direct provision of an endogenous elastase inhibitor may involve administering to the subject the endogenous elastase inhibitor itself.

Merely by way of example, indirect provision of an endogenous elastase inhibitor may involve administering a compound which will result in increased expression of an endogenous elastase inhibitor in the subject. Alternatively, the indirect provision of an endogenous elastase inhibitor may involve administering a nucleic acid which encodes an endogenous elastase inhibitor.

The first and second aspects of the disclosure respectively relate to medical uses and methods of treatment for the promotion of muscle regeneration and muscle fiber stability in the treatment of myopathies. Such a promotion of muscle regeneration and muscle fiber stability may be due to the ability of elastase inhibitors to protect muscle progenitor cell regenerative potential. In this context, the promotion of muscle regeneration and muscle fiber stability refers to any clinical improvement in muscle function, which may be demonstrated by increased muscle strength, increased muscle mass, reduced pseudohypertrophy and/or reduced muscle atrophy. The clinical improvement may be compared to the state that otherwise occurs in an untreated myopathy.

Accordingly, in one embodiment muscle regeneration and muscle fiber stability may be considered to be promoted if the muscle strength and/or muscle mass is increased by at least 5%, at least 10%, at least 20%, at least 30%, at least 40%, at least 50%, at least 60%, at least 70% or more as compared to control or the subjects own muscle strength and/or muscle mass prior to treatment. Methods for testing muscle strength may include a walk or run test, but other methods will be known to the skilled person. Methods for testing muscle mass include, for example, determining 24 hour urinary creatinine levels, or body scanning using methods such as Dual-Energy X-Ray Absorptiometry (DEXA), Total Body Potassium (TBK), Magnetic Resonance Imaging (MRI), Total Body Electrical Conductivity (TOBEC), and Computed Tomography (CT).

In a suitable embodiment, muscle regeneration and muscle fiber stability may be considered to be promoted if pseudohypertrophy and/or muscle atrophy is decreased by at least 5%, at least 10%, at least 20%, at least 30%, at least 40%, at least 50%, at least 60%, at least 70% or more as compared to control or pseudohypertrophy and/or muscle atrophy observed in the subject prior to treatment. A decrease in pseudohypertrophy may be observed by a reduction in size of the calf muscle. A decrease in muscle atrophy may, for example, be determined histologically. Other methods for assessing pseudohypertrophy and/or muscle atrophy will be known to the skilled person.

The ability of elastase inhibitors to promote muscle regeneration and muscle fiber stability in the treatment of myopathies is based on the inventor's surprising finding that elastase inhibitors have a protective effect on the regenerative potential of muscle progenitor cells associated with myopathies and on the stability of the muscle fiber itself.

The term "muscle progenitor cells" as used herein, refers to cells selected from the group consisting of: satellite cells, pericytes, myoendothelial cells, side population cells, mesenchymal stem cells, and myoblasts. It will be appreciated that references to muscle progenitor cells within the present disclosure may be interpreted as referring to individual populations of such cells (for example solely satellite cells or solely myoblast cells), or to combinations of two, three, four, five, or six of these cell types.

Such a protective effect on muscle progenitor cells in subjects with impaired muscle regeneration due to a myopathy such as Duchenne muscular dystrophy, may result in an increase in muscle progenitor cells. Thus, muscle regeneration may be considered to be promoted if the number of muscle progenitor cells has increased by at least 5%, at least 10%, at least 20%, at least 30%, at least 40%, at least 50%, at least 60%, at least 70% or more as compared to the number of muscle progenitor cells in a relevant control (such as a sample from the same subject prior to treatment).

Suitably the elastase inhibitors achieve their therapeutic effect through promoting muscle regeneration by protecting muscle progenitor cells and/or their ability to differentiate and fuse into muscle fibers. The inventors believe that by protecting muscle progenitor cell regenerative potential, elastase inhibitors enable or enhance the growth of new or existing muscle fibers, particularly in individuals diagnosed with a myopathy. Accordingly, muscle regeneration may be considered to be promoted if the number of new muscle fibers is increased by at least 5%, at least 10%, at least 20%, at least 30%, at least 40%, at least 50%, at least 60%, at least 70% or more. Similarly, muscle regeneration may be considered to be promoted if the thickness of existing muscle fibers is increased by at least 5%, at least 10%, at least 20%, at least 30%, at least 40%, at least 50%, at least 60%, at least 70% or more. The number of new muscle fibers, as well as the thickness of existing muscle fibers may, for example, be determined through histological analysis of muscles pre and post exposure to elastase inhibitors. Suitably, muscle regeneration may be considered to be promoted if muscle fiber diameter has increased by at least 5%, at least 10%, at least 20%, at least 30%, at least 40%, at least 50%, at least 60%, at least 70% or more. Muscle fiber diameter may be determined using various methods known to the skilled person, including measuring the minimum Feret diameter or the area of a muscle fiber cross-section.

The inventors believe that the protective effect of elastase inhibitors on muscle progenitor cell regenerative potential may prevent elastase induced loss of muscle fibers. Muscle fiber loss may result from a reduction in the number of muscle progenitor cells, reduction in muscle progenitor cell proliferation (in particular myoblast proliferation), reduction in muscle progenitor cell differentiation (in particular myoblast differentiation), a reduction in myoblast fusion and/or a reduction in myotube growth.

Therefore, in the context of the present disclosure, the term "promotion of muscle regeneration" is intended to include one or more protective effects on muscle progenitor cells. Such protective effects may be selected from the group consisting of: increased muscle progenitor cell number, increased muscle progenitor cell proliferation, increased muscle progenitor cell differentiation, increased muscle progenitor cell survival, increased myoblast fusion, and/or increased myotube growth.

In one embodiment, muscle regeneration may be considered to be promoted if muscle progenitor cell number, muscle progenitor cell proliferation, muscle progenitor cell differentiation, muscle progenitor cell survival, myoblast fusion and/or myotube growth is increased by at least 5%, at least 10%, at least 20%, at least 30%, at least 40%, at least 50%, at least 60%, at least 70% or more.

In one embodiment, muscle regeneration may be considered to be promoted if muscle fibrosis is reduced. Suitably, muscle fibrosis may be reduced by at least 5%, at least 10%, at least 20%, at least 30%, at least 40%, at least 50%, at least 60%, at least 70% or more. More suitably, muscle regeneration may be considered to be promoted if muscle fibrosis is reduced by at least 30%. The skilled person will appreciate that there are various methods for determining muscle fibrosis. Such methods may include a muscle biopsy to measure the extent of muscle fibrosis (for example pre- and post-treatment).

An element of treating myopathies is the preservation of muscle fiber stability. Muscle fiber stability refers to the dystrophin-associated complex acting as a master node in muscle fibers that integrate cytoskeletal organization and cellular signaling at the muscle periphery, as well as providing sarcolemmal stabilization and contractile three transmission to the extracellular region. Specifically, the dystrophin-associated surface complex forms an organizing node that is majorly involved in (i) the provision of sarcolemmal membrane integrity via a stabilizing linkage between the intracellular actin cytoskeleton and the extracellular matrix protein laminin, (ii) the establishment of a molecular scaffold and anchoring system for ion channels and enzymes to mediate cellular signaling processes (iii) the organization of actin filament attachment and its associated cytoskeletal network, and (iv) the mediation of lateral force transmission from sarcomeric contraction to the endomysium and its connected layers of the extracellular matrix. The preservation of these complexes is an indicator of the treatment of the myopathy.

The term "subject" as used herein, refers to any individual who may benefit from the promotion of muscle regeneration in the treatment of a myopathy. The subject may be a human subject. The human subject may be a child.

An individual who may benefit from the promotion of muscle regeneration may have symptoms associated with a myopathy, such as muscle weakness and/or reduced muscle mass. Alternatively, the subject may be asymptomatic but at risk of developing such symptoms. Symptoms associated with muscle weakness and/or reduced muscle mass include, but are not limited to a difficulty in walking, difficulty in running, difficulty in standing up and/or difficulty in breathing.

Disorders particularly associated with muscle weakness and/or impaired muscle regeneration include myopathies, in particular myopathies associated with muscle inflammation. Such myopathies are characterized by increased infiltration of white blood cells (in particular neutrophils) in the muscles. By way of example, a myopathy associated with muscle inflammation may be determined by histological analysis (such as haematoxylin and eosin staining) of a muscle biopsy. Merely by way of example, myopathies associated with muscle inflammation may be selected from the group consisting of polymyositis, dermatomyositis, inclusion body myositis, congenital inflammatory myopathy and muscular dystrophy.

Accordingly, a subject may be any individual diagnosed with, or at risk of developing a myopathy. Suitably the subject may be an individual diagnosed with, or at risk of developing a myopathy associated with muscle inflammation. In particular, the subject may be diagnosed with, or at risk of developing polymyositis, dermatomyositis, inclusion body myositis, congenital inflammatory myopathy or a muscular dystrophy. A suitably muscular dystrophy may be selected from the group consisting of: Duchenne muscular dystrophy, Becker muscular dystrophy, congenital muscular dystrophy, distal muscular dystrophy, Emery-Dreifuss muscular dystrophy, facioscapulohumeral muscular dystrophy, limb-girdle muscular dystrophy, myotonic muscular dystrophy and oculopharyngeal muscular dystrophy. Suitably, the subject may be diagnosed with, or at risk of developing Duchenne muscular dystrophy. Other suitable myopathies include diabetic myopathy, Chronic obstructive pulmonary disease (COPD) induced myopathy and/or atrophy, infection-induced myopathy and/or atrophy, cancer-induced myopathy and/or cachexia, immobility-induced atrophy and sarcopenia.

In a suitable embodiment, a subject may be considered at risk, for example, due to a known predisposition, such as the presence of a mutation (for example the DMD gene) and/or a familial history. Suitably, a subject at risk of developing symptoms associated with impaired muscle regeneration may be asymptomatic.

The medical uses and methods of treatment of the first and second aspects of the disclosure are useful in the treatment of myopathies. In a suitable embodiment, the uses and methods of the first and second aspects of the disclosure may be employed in the treatment of muscular dystrophy. Suitably, the muscular dystrophy may be Duchenne muscular dystrophy.

The term "treatment" as used herein refers to an intervention which prevents the progression, or reduces partially or completely the clinical symptoms associated with a myopathy, such as muscular dystrophy, in a subject. Accordingly, the term "treatment" encompasses not only the therapeutic use of elastase inhibitors in a subject with the symptoms of a myopathy, such as muscular dystrophy, but also the use of elastase inhibitors in the treatment of a subject who does not exhibit the symptoms of the myopathy. Such uses may be of particular relevance to an asymptomatic subject known to carry a mutation which increases the subject's likelihood of developing a myopathy, such as muscular dystrophy.

The term "a therapeutically effective amount" as used herein, refers to an amount of elastase inhibitor, that when provided to the subject with a myopathy, is sufficient to promote muscle regeneration and muscle fiber stability in the subject. Merely by way of example promotion of muscle regeneration and muscle fiber stability may be demonstrated by a clinical improvement of symptoms associated with reduced muscle regeneration and muscle fiber instability. Other ways in which promotion of muscle regeneration may be demonstrated are considered elsewhere in this specification. By way of example, an improvement in symptoms may be demonstrated by increased muscle strength, increased resistance to fatigue and contraction-induced injury, and/or increased muscle mass.

Additionally or alternatively, promotion of muscle regeneration and muscle fiber stability may be demonstrated by an improvement in muscle pathology. Suitably, an improvement in muscle pathology may be demonstrated by a decrease in muscle fibrosis, a decrease in muscle inflammation and an increase in muscle progenitor cell number, increase in muscle progenitor cell proliferation, increase in muscle progenitor cell differentiation, increase in myoblast fusion, increase in myotube growth, and/or increase in muscle progenitor cell survival.

It will be appreciated that the therapeutically effective amount may vary depending on various factors, including the type of elastase inhibitor. Different types of elastase inhibitors will have a different half-life and/or bioavailability, which may alter the therapeutically effective amount.

The therapeutically effective amount may also vary depending on the subject's age, weight and/or gender.

By way of example, a therapeutically effective amount of the elastase inhibitor sivelestat may be between 1 and 10 mg/kg/day, suitably between 3 and 7 mg/kg/day, more suitable approximately 5 mg/kg/day. By way of example, a therapeutically effective amount of the elastase inhibitor Depelestat may be between 0.5 and 7 mg/kg/day, suitably between 1.5 and 5 mg/kg/day, more suitably approximately 3 mg/kg/day. By way of example, a therapeutically effective amount of the elastase inhibitor Alvelestat may be between 10 and 150 mg/day, suitably 50 and 100 mg/day, more suitably approximately 60 mg/day.

The third aspect is based on the inventors' surprising finding that subjects with a myopathy, in particular with muscular dystrophy such as Duchenne muscular dystrophy, may have higher levels of elastase activity as compared to individuals without such a disease. The inventors believe that this finding may be of particular utility in determining or monitoring the effectiveness of a treatment in a subject with a myopathy.

Accordingly, the third aspect relates to a method of determining the effectiveness of a treatment in a subject with a myopathy, the method can include the steps of:
  measuring elastase activity in a sample from the subject;
  comparing the elastase activity in the subject's sample to
    a reference value, and
  thereby determining the effectiveness of the treatment.

It will be appreciated that the reference value may be based upon the elastase activity measured either in one or more samples from a control individual(s), or in one or more samples from a subject(s) diagnosed with a myopathy and who did not receive treatment.

In one embodiment, the reference value is based upon the elastase activity measured in one or more samples from control individual(s). In such an embodiment, if the elastase activity measured in a sample from a subject treated for a myopathy approximates the elastase activity measured in a sample(s) from the control individual(s), it provides an indication that the treatment is effective.

By the same token, if the elastase activity measured in a sample from a subject treated for a myopathy does not approximate the elastase activity measured in a sample from a control individual, it may be an indication that the treatment is not effective. In the context of the present disclosure the term "approximates" may be taken as referring to elastase activity which is within 0.5-fold or less, 0.4-fold or less, 0.3-fold or less, 0.2-fold or less, 0.1-fold or less, or 0.05-fold or less, from the reference value.

In another embodiment, the reference value is based upon the elastase activity measured in a sample(s) from an individual(s) with a myopathy who has not received treatment. Suitably, the individual with a myopathy may be the subject themselves prior to receiving treatment. In such an embodiment, if the elastase activity measured in a sample from a subject treated for a myopathy approximates the elastase activity measured in a sample from an individual with a myopathy, it may be an indication that the treatment is not effective.

Similarly, if the elastase activity measured in the sample from the subject treated for a myopathy is lower than the elastase activity measured in the sample from an untreated individual with a myopathy, it may be an indication that the treatment is effective. It will be appreciated that any reduction in elastase activity as compared to a reference value based upon elastase activity in a sample from an individual with a myopathy may be an indication that the treatment is effective. Suitably, elastase activity that is at least 0.05-fold, at least 0.1-fold, at least 0.2-fold, at least 0.3-fold, at least 0.4-fold, at least 0.5-fold or more, lower than the reference value, may be an indication that the treatment is effective.

Methods for measuring elastase activity will be known to the skilled person. By way of example, elastase activity may be measured with the use of the fluorigenic peptide Suc-Ala-Ala-Ala-AMC as further explained in the Examples section.

In the context of the present disclosure, the term sample refers to any suitable sample that provides an indication as to the elastase activity in the subject. The sample may be a solid sample or a body fluid sample. Suitably, the sample may be a fluid sample selected from the group consisting of: a blood sample (for example, a whole blood sample, a blood plasma sample, or a serum sample) and a urine sample. More suitably, the sample is a serum sample. A suitable solid sample may be a muscle biopsy.

In one embodiment the pharmaceutical composition may comprise an elastase inhibitor and a pharmaceutically acceptable carrier. Suitably, the pharmaceutical composition may comprise any elastase inhibitor disclosed herein. More suitably, the elastase inhibitor may be selected from the group consisting of: Alvelestat, sivelestat, dociparstat, lonodelestat, tiprelestat, depelestat, lodelaben, telmesteine, BAY85-8501, BAY-678, Freselestat and AZD9819.

The "term pharmaceutically acceptable carrier" as used herein refers to any suitable diluent, excipient, or a combination thereof, suitable for administration into a subject. A pharmaceutically acceptable carrier may be an organic or inorganic substance, which facilities the delivery of an elastase inhibitor to the subject.

In a suitable embodiment, a pharmaceutical composition of the disclosure may further comprise a pharmaceutically acceptable concentration of salt, buffering agents, and compatible carriers. The compositions may also include antioxidants and/or preservatives. Suitable antioxidants may be selected from the group consisting of: mentioned thiol derivatives (e.g. thioglycerol, cysteine, acetylcysteine, cystine, dithioerythreitol, dithiothreitol, glutathione), tocopherols, butylated hydroxyanisole, butylated hydroxytoluene, sulfurous acid salts (e.g. sodium sulfate, sodium bisulfite, acetone sodium bisulfite, sodium metabisulfite, sodium sulfite, sodium formaldehyde sulfoxylate, sodium thiosulfate) and nordihydroguaiareticacid. Suitable preservatives may for instance be phenol, chlorobutanol, benzylalcohol, methyl paraben, propyl paraben, benzalkonium chloride and cetylpyridinium chloride.

The pharmaceutical composition of the present disclosure may be for administration to the subject via any suitable route. A suitable route of administration may be selected from the group consisting of: oral, topical, intramuscular, intravenous, intraperitoneal and subcutaneous. Other methods for administering pharmaceutical compositions will be known to the skilled in the art.

In one embodiment, the pharmaceutical composition of the present disclosure is for oral administration. Suitable oral administration forms include solid dosage forms, such as capsules, tablets, powders and granules. In such solid dosage forms, the elastase inhibitor may be mixed with at least one inert, pharmaceutically acceptable excipient or carrier such as sodium citrate or dicalcium phosphate and/or one or more: a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules and tablets, the dosage form may also comprise buffering agents. Solid compositions of a similar type may also be employed as fillers in soft and hard-filled gelatin capsules using such excipients as lactose or milk sugar as well as high molecular weight polyethylene glycol, for example.

Suitably, oral formulations may contain a dissolution aid. The dissolution aid is not limited as to its identity so long as it is pharmaceutically acceptable. Examples include non-ionic surface agents, such as sucrose fatty acid esters, glycerol fatty acid esters, sorbitan fatty acid esters (e.g., sorbitan trioleate), polyethylene glycol, polyoxyethylene hydrogenated castor oil, polyoxyethylene sorbitan fatty acid esters, polyoxyethylene alkyl ethers, methoxypolyoxyethylene alkyl ethers, polyoxyethylene alkylphenyl ethers, polyethylene glycol fatty acid esters, polyoxyethylene alkylamines, polyoxyethylene alkyl thioethers, polyoxyethylene polyoxypropylene copolymers, polyoxyethylene glycerol fatty acid esters, pentaerythritol fatty acid esters, propylene glycol monofatty acid esters, polyoxyethylene propylene glycol monofatty acid esters, polyoxyethylene sorbitol fatty acid esters, fatty acid alkylolamides, and alkylamine oxides; bile acid and salts thereof (e.g., chenodeoxycholic acid, cholic acid, deoxycholic acid, dehydrocholic acid and salts thereof, and glycine or taurine conjugate thereof); ionic surface agents, such as sodium laurylsulfate, fatty acid soaps, alkylsulfonates, alkylphosphates, ether phosphates, fatty acid salts of basic amino acids; triethanolamine soap, and alkyl quaternary ammonium salts; and amphoteric surface agents, such as betaines and aminocarboxylic acid salts. Pharmaceutical compositions of the disclosure, comprising an elastase inhibitor may also be in microencapsulated form, if appropriate, with one or more of the above-mentioned excipients.

In one embodiment, the pharmaceutical composition is for administration in liquid dosage form. Liquid dosage forms for oral administration include pharmaceutically acceptable emulsions, solutions, suspensions, syrups and elixirs. In addition to the elastase inhibitor, the liquid dosage forms may contain inert diluents commonly used in the art such as water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan and mixtures thereof. Besides inert diluents, the oral compositions may also include adjuvants such as wetting agents, emulsifying and suspending agents, sweetening, flavouring and perfuming agents. Suspensions, in addition to the elastase inhibitor, may contain suspending agents such as ethoxylated isostearyl alcohols, polyoxyethylene sorbitol and sorbitan esters, microcrystalline cellulose, aluminium metahydroxide, bentonite, agar-agar, and tragacanth and mixtures thereof.

In a suitable embodiment, the pharmaceutical composition is for intramuscular administration. In such an embodiment, a sterile pharmaceutical composition may be especially desirable. A sterile pharmaceutical composition may be obtained, for example, by filtration though sterile filtration membranes.

In a suitable embodiment, the pharmaceutical composition of the present disclosure may be for sustained release of the elastase inhibitor. Such a pharmaceutical composition may comprise semipermeable matrices of solid hydrophobic polymers containing the elastase inhibitor, wherein the matrices are in the form of shaped articles, films or microcapsules. Examples of sustained-release matrices include polyesters, hydrogels, copolymers of L-glutamic acid and gamma ethyl-L-glutamate, non-degradable ethylene-vinyl acetate degradable lactic acid-glycolic acid copolymers such as the LUPRON Depot™ (injectable microspheres composed of lactic acid-glycolic acid copolymer and leuprolide acetate), and poly-D-(−)-3-hydroxybutyric acid.

In another embodiment, the disclosure is directed to methods for prevention of glucocorticoid toxicity that comprise administering to a subject in need thereof an elastase inhibitor in combination with a glucocorticoid. The method for prevention of glucocorticoid toxicity can be effected with the elastase inhibitor, which promotes muscle regeneration and muscle fiber stability by protecting muscle progenitor cells and mature muscle fibers. This elastase inhibitor can be provided in an amount sufficient to protect the regenerative potential of muscle progenitor cells and the stability of muscle fibers. Further, the addition of an elastase inhibitor to a glucocorticoid further enhances the glucocorticoid's anti-inflammatory activity.

Figures 12A, 12B, 12C, 12D, 12E, 12F:
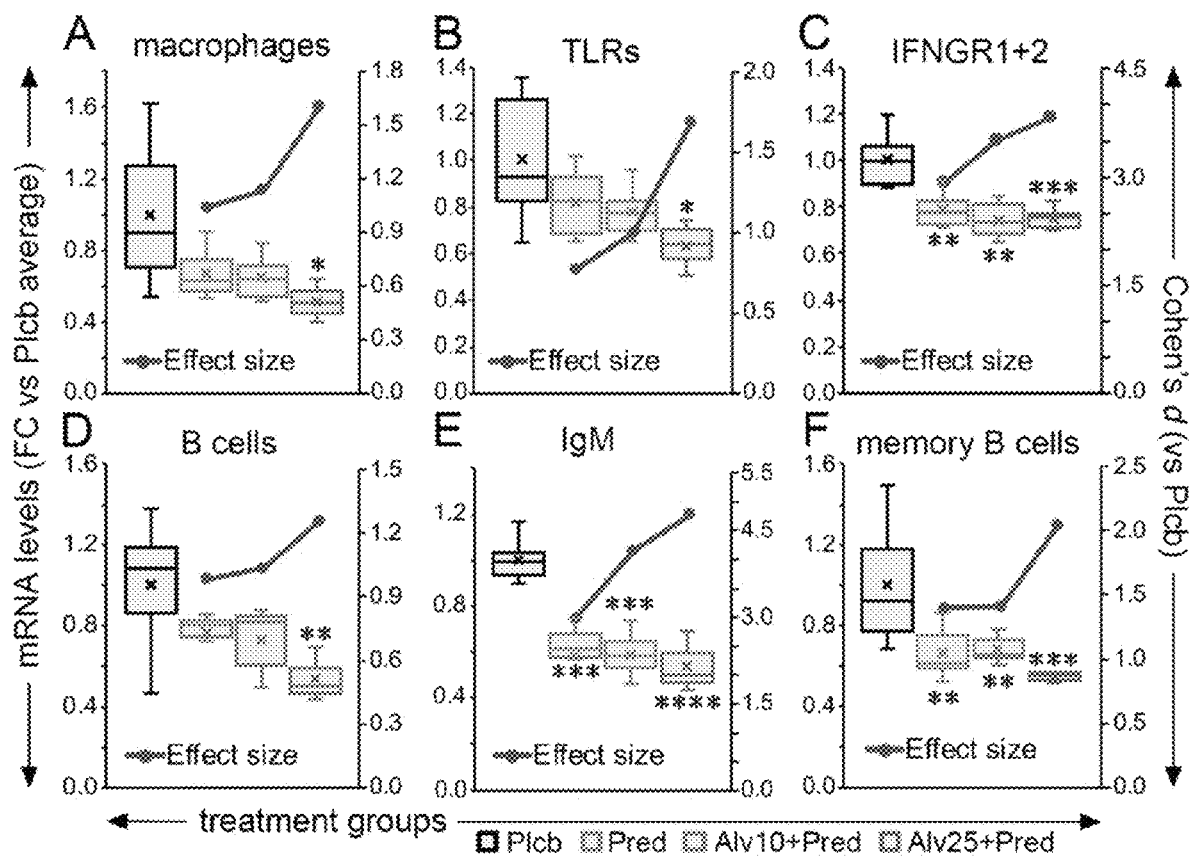
FIGS. 12A-12F are illustrations of mRNA levels for various markers.

This was totally unexpected prior to this disclosure, because the elastase inhibitor alone does not decrease inflammation in fact, if anything, it increases it. This is further shown and described in FIG. 12 below, which illustrates this potentiation of the glucocorticoid anti-inflammatory activity by the addition of the elastase inhibitor.

In one embodiment, the elastase inhibitor is a neutrophil elastase inhibitor. The elastase inhibitor can be any suitable elastase inhibitor, such as those selected from the group consisting of: Alvelestat, Elastatinal, sivelestat, dociparstat, lonodelestat, tiprelestat, depelestat, lodelaben, telmesteine, BAY85-8501, BAY-678, Freselestat, AZD9819, GW-31 1616A, POL6014, SSR 69071, GW475151, ICI 200,880 and AX-9657, Midesteine, 1-(3-methylbenzoyl)-1H-indazole-3-carbonitrile, Elastase inhibitor II, Elastase inhibitor III, Elastase inhibitor V, N-(Methoxysuccinyl)-Ala-Ala-Pro-Val-chloromethyl ketone, 1,4-diarylpyrimidopyridazinyldione or a derivative thereof, 2-pyrazinone or a derivative thereof, 2-pyridone or a derivative thereof, pyridyl-3-yl-benzo[d][1,3]oxazin-4-one or a derivative thereof, 3,4,6,7-tetrahydro-1H-pyrrolo[3,4-d]pyrimidine-2,5-dione or derivative thereof, 4-(4-Cyano-2-thioaryl)-dihydropyrimidone or a derivative thereof, 4-(4-cyanophenyl)-1-(3-trifluoromethylphenyl)-3,4,6,7-tetrahydro-1H-pyrrolo[3,4-d]pyrimidine-2,5-dione or a derivative thereof, Azetidine-2, 4-dione or a derivative thereof, Benzoxazinone or a derivative thereof, Dihydropyrimidone or a derivative thereof, functionalized N-amino-4-imidazolidinone, N-Benzoyl pyrazole or a derivative thereof, Tetrazolopyrimidine or a derivative thereof, Serpinbl, Elafin, Alpha-1-antitrypsin, Protein AMBP, Antileukoproteinase, Eppin and Alpha-2-macroglobulin, and wherein the glucocorticoid is selected from the group consisting of methyl prednisolone, prednisolone, deflazacort, fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-1,3-hydroxy-16α-methyl-3-oxo-androsta-1,4-diene-17β-carbothioic acid S-fluoromethyl ester (fluticasone furoate), 6α,9α-difluoro-1,3-hydroxy-16α-methyl-3-oxo-17α-propionyloxy-androsta-1,4-diene-17β-carbothioic acid S-(2-oxo-tetrahydro-furan-3S-yl) ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-1,3-hydroxy-16α-methyl-17α-(1-methycyclopropylcarbonyl)oxy-3-oxo-androsta-1,4-diene-17β-carbothioic acid S-fluoromethyl ester, beclomethasone esters, 17-propionate ester, 17,21-dipropionate ester, budesonide, flunisolide, mometasone esters, mometasone furoate, triamcinolone acetonide, rofleponide, ciclesonide (16α,17-[[(R)-cyclohexylmethylene]bis(oxy)]-11β,21-dihydroxy-pregna-1,4-diene-3,20-dione), butixocort propionate, RPR-106541, ST-126, fluticasone propionate, 6α,9α-difluoro-1,3-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-1,3-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

In other embodiments, the elastase inhibitor can be selected from the group consisting of: Alvelestat, Elastatinal, sivelestat, dociparstat, lonodelestat, tiprelestat, depelestat, lodelaben, telmesteine, BAY85-8501, BAY-678, Freselestat and AZD9819, and wherein the glucocorticoid is selected from the group consisting of methyl prednisolone, prednisolone, and deflazacort, prednisone, dexamethasone, cortisone, hydrocortisone, mifepristone, RU28362, corticosterone, beclomethasone, betamethasone, budesonide, triamcinolone, fluticasone, mometasone, ciclesonide, flunisolide, clobetasol, vamorolone.

Additional embodiments of the methods described herein are provided in the enclosed appendix.

EXAMPLES

The present disclosure is further illustrated by the following non-limiting example:

Example 1

Figure 1F:
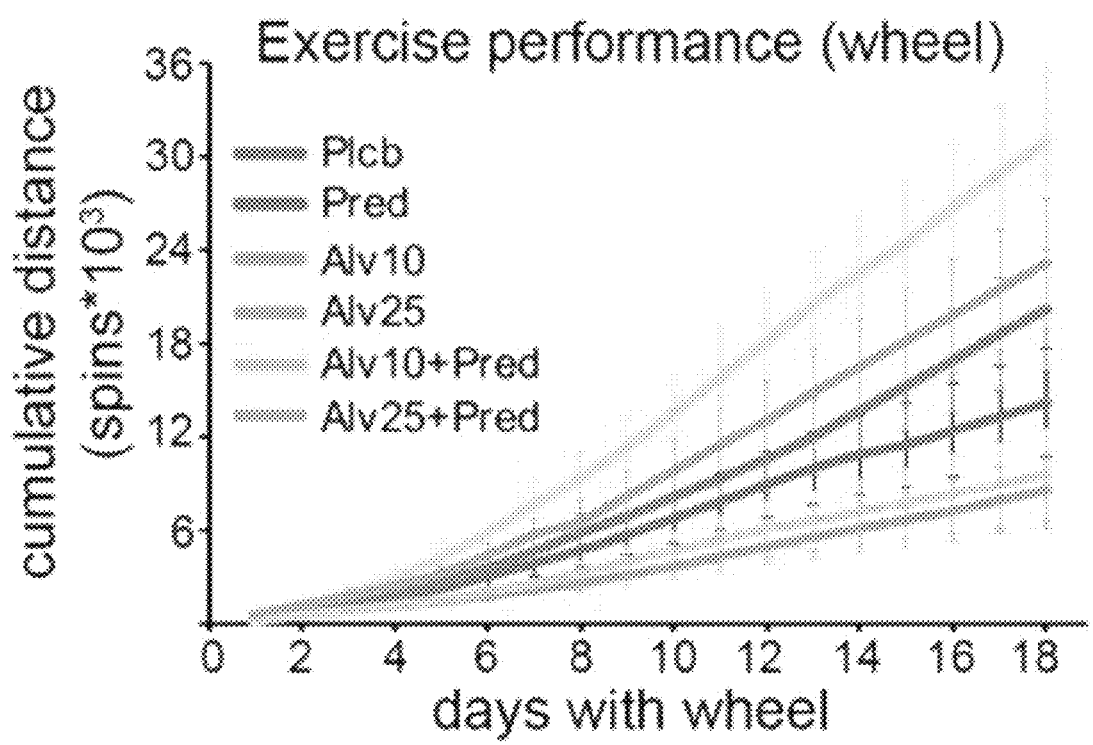
FIG. 1F is a graphical illustration of exercise performance of the tested mice over time.

FIG. 1F is a graphical illustration of data gathered from in vivo testing efficacy of a placebo, as compared to the elastase inhibitor Alvelestat, alone at various administration concentrations, and in combination with the glucocorticoid prednisolone at various administration concentrations. In this, and the following figures, the abbreviation "Plcb" refers to administration of a placebo, the abbreviation "Pred" refers to administration of prednisolone at 1 mg/kg/day, the abbreviation "Alv10" refers to the administration of the elastase inhibitor alvelestat at 10 mg/kg/day, and the abbreviation "Alv25" refers to the administration of the elastase inhibitor alvelestat at 25 mg/kg/day.

The administration of the various compounds occurred over a 12-week period, in a controlled randomized, double blinded test using dystrophin-deficient mice (mdx4cv strain). In FIG. 1F, beginning during the tenth week of the test, the mice were exposed to an activity wheel, with the cumulative distance plotted on the y-axis and the number of days spent with the exercise wheel plotted on the x-axis. As can be seen, the Alv10+ Pred cohort travelled further than any other cohort over the course of exposure to the exercise wheel.

Figure 2:
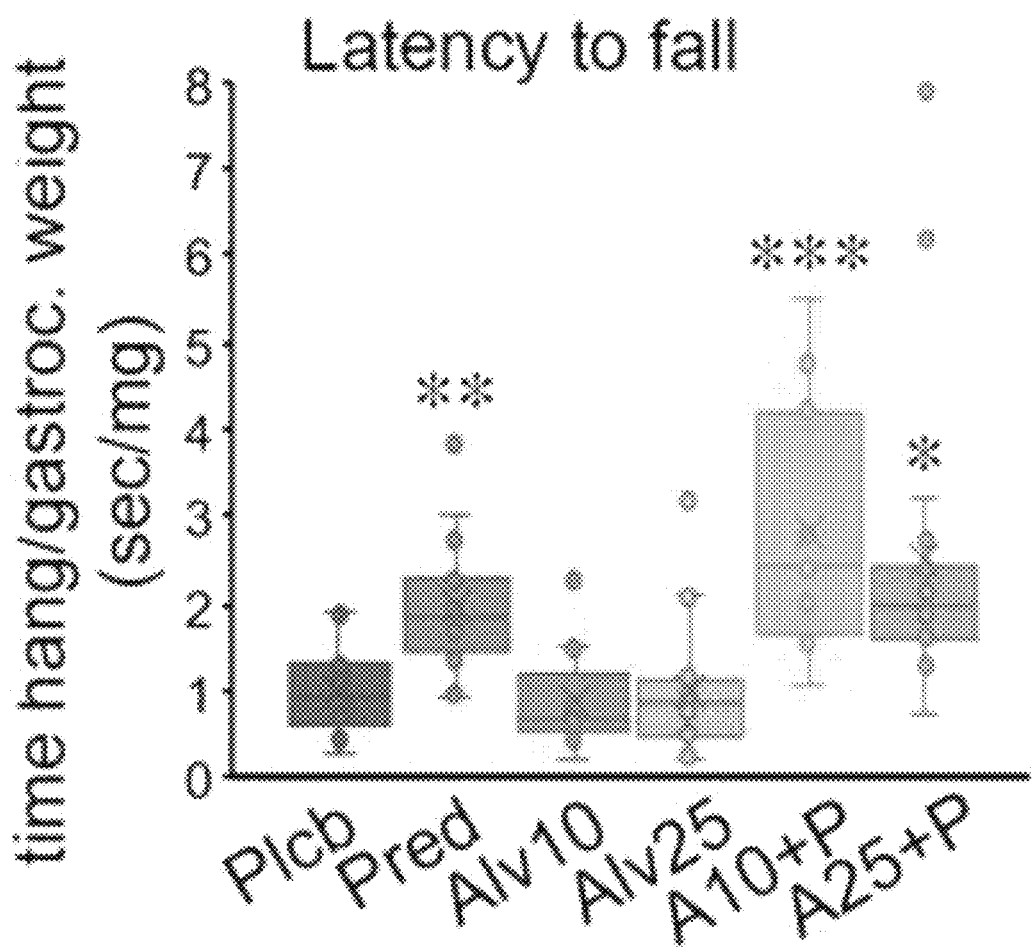
FIG. 2 is a graphical illustration of the latency to fall of the tested mice in a four-limb hanging test.

At several points during the 12 week testing period the mice were subject to the four-limb hanging test, with the results shown in FIG. 2. In FIG. 2, plotted on the y-axis is the time the animal spent hanging divided by their muscle weight. As can be seen, the Alv10+Pred cohort had a longer latency during the test as compared to the other cohorts.

Figure 3:
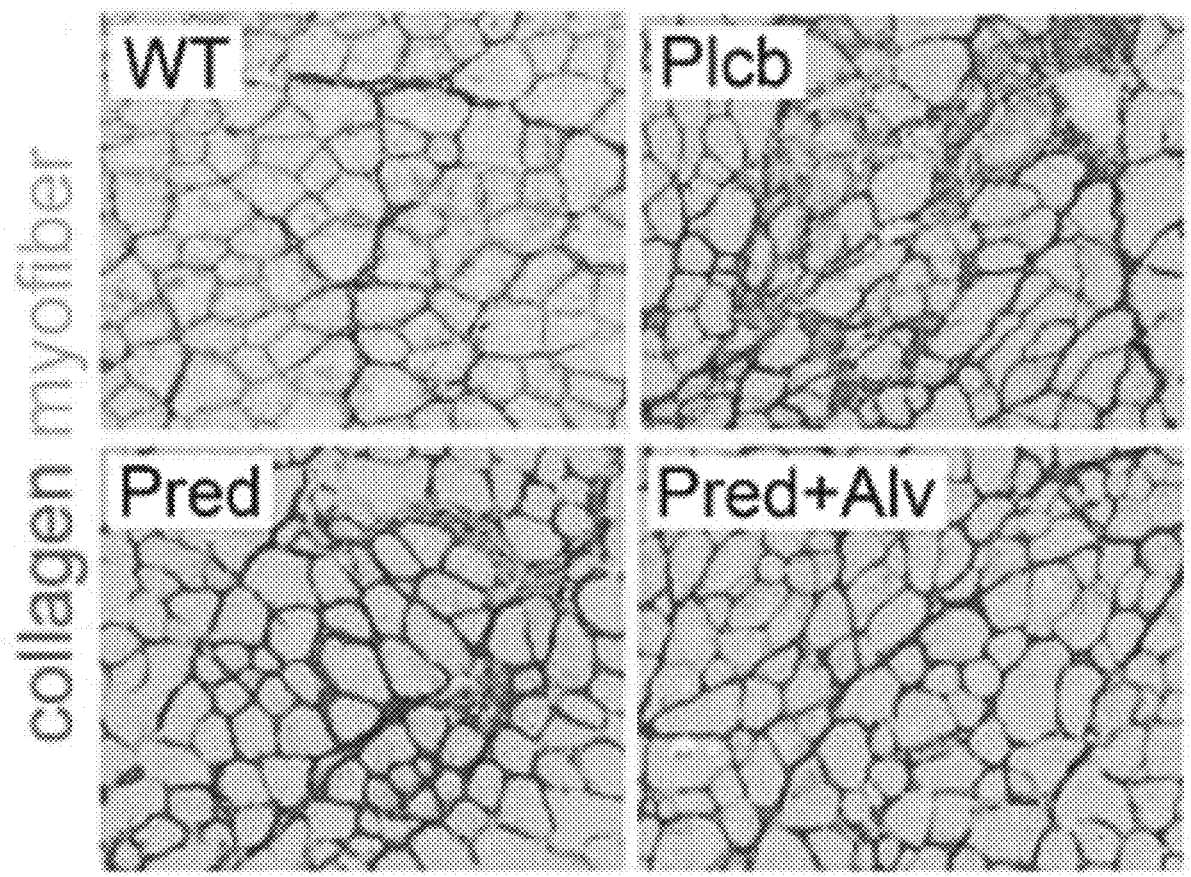
FIG. 3 are images of collagen and myofiber structures of various cohorts of mice.
Figure 4:
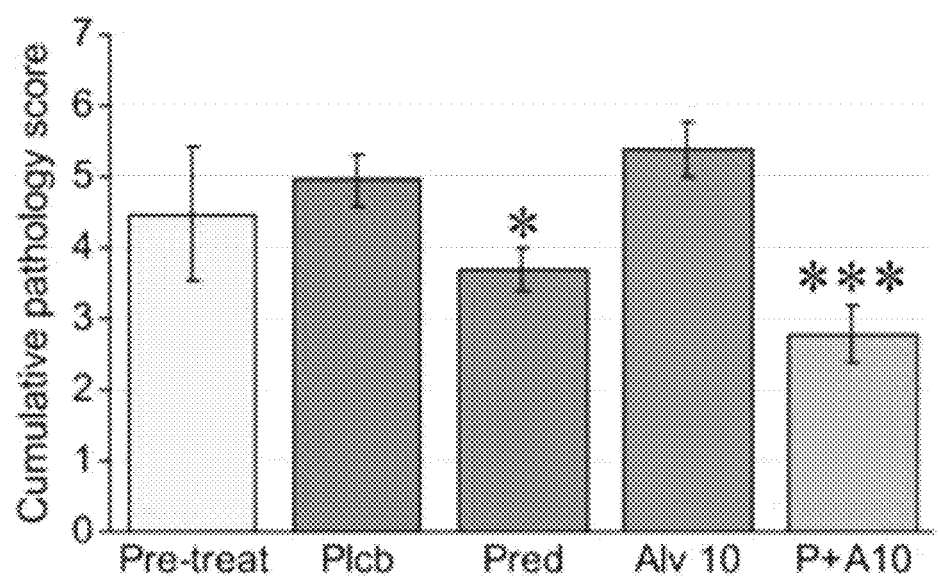
FIG. 4 is a graphical illustration of the triceps pathology score for various cohorts of mice.
Figure 5:
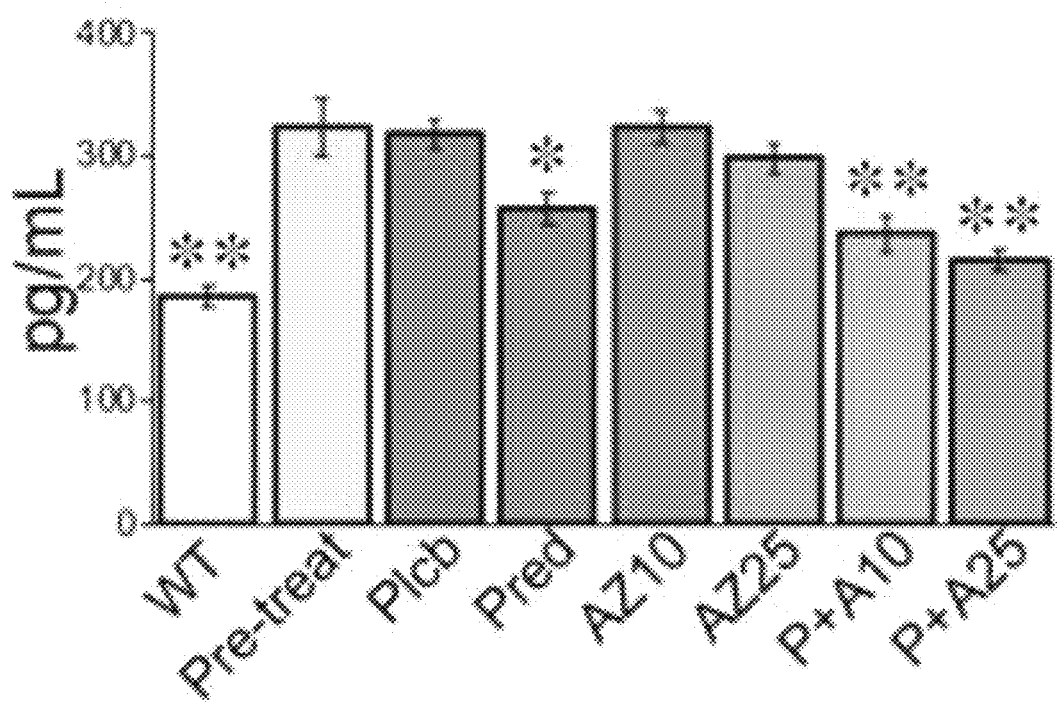
FIG. 5 is a graphical illustration of active transforming growth factor beta (TGF-β) concentrations in muscle for various cohorts of tested mice.

As can be seen from FIG. 3, images were captured to demonstrate the difference between collagen (red) and muscle fiber (yellow) structures between a wild type mouse, as compared to a dystrophin-deficient, treated mouse, at the conclusion of the 12 week administration period. FIG. 4 is a graphical illustration of the cumulative triceps pathology score for various cohorts of tested mice, at the conclusion of the 12 week administration period. FIG. 5 is a graphical illustration of active transforming growth factor beta (TGF-β) concentrations for various cohorts of tested mice, at the conclusion of the 12 week administration period.

One conclusion that can be drawn from FIGS. 3-5 is that the combination of an elastase inhibitor in combination with a glucocorticoid further decreases inflammation and fibrosis in the tested mice.

Figure 6:
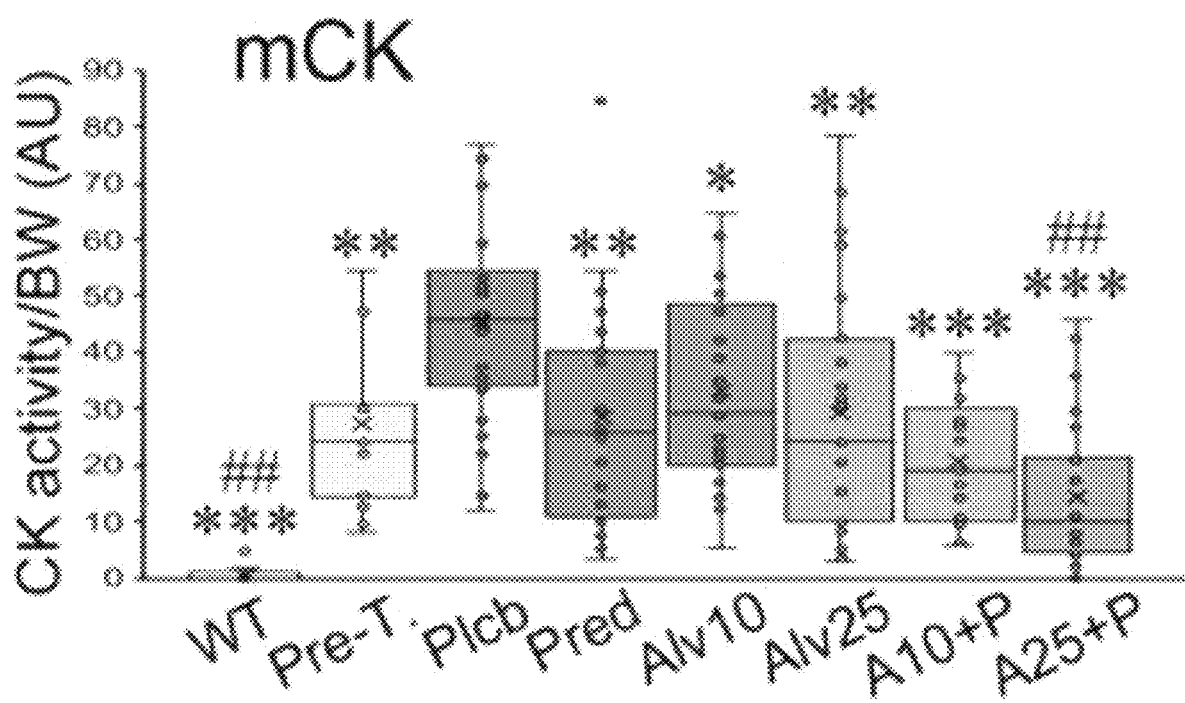
FIG. 6 is a graphical illustration of muscle creatine kinase (mCK) activity levels for various cohorts of tested mice.
Figure 7:
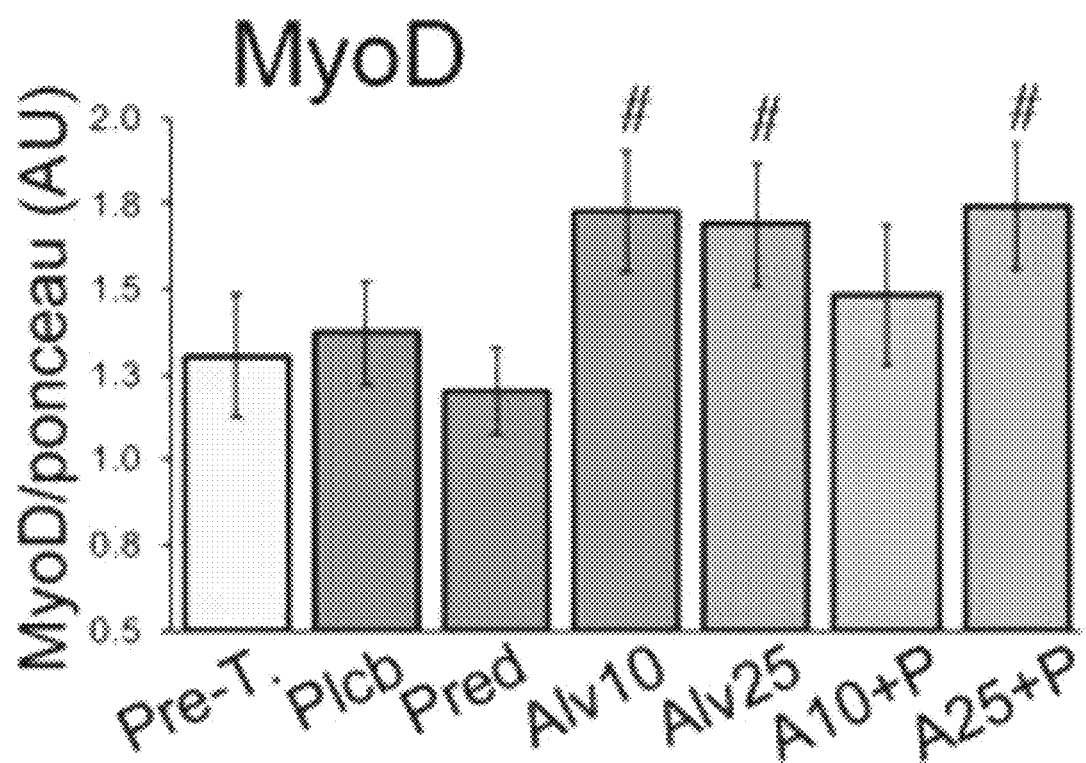
FIG. 7 is a graphical illustration of MyoD protein levels for various cohorts of tested mice.
Figure 8:
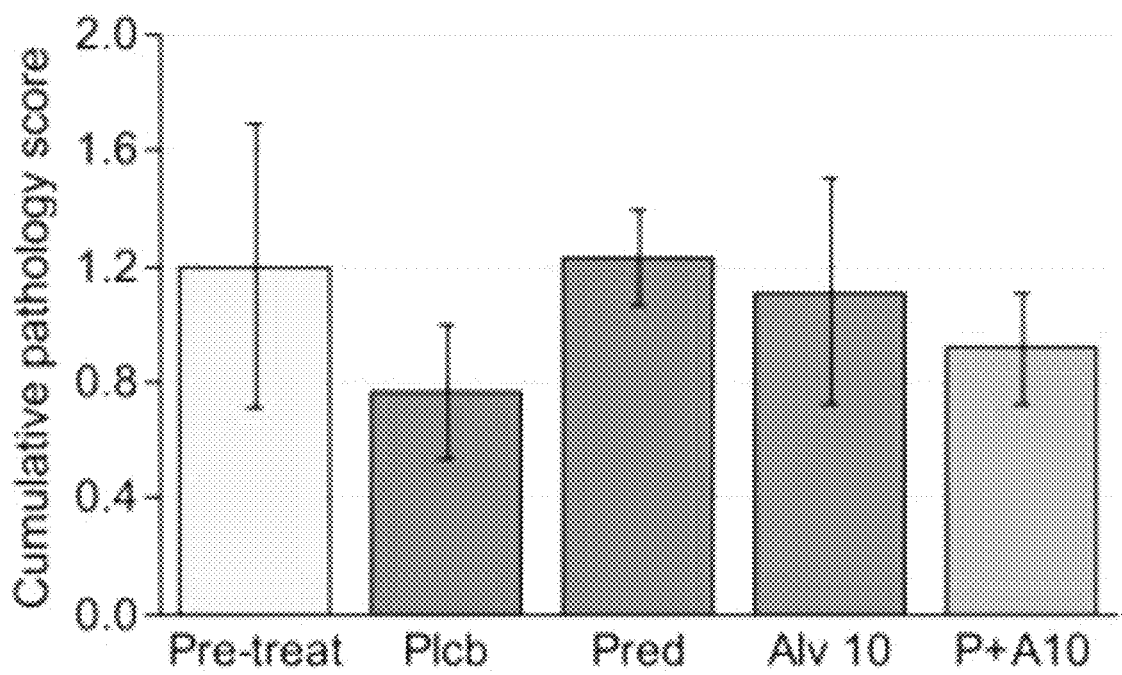
FIG. 8 is a graphical illustration of liver pathology score for various cohorts of tested mice.

FIG. 6 is a graphical illustration of muscle creatine kinase (mCK) activity for various cohorts of tested mice (including mice pre-treatment with any elastase inhibitor or glucocorticoid) at the conclusion of the 12 week administration period. FIG. 7 is a graphical illustration of MyoD protein levels for various cohorts of tested mice (including mice pre-treatment with any elastase inhibitor or glucocorticoid) at the conclusion of the 12 week administration period. FIG. 8 is a graphical illustration of liver pathology scores for various cohorts of tested mice (including mice pre-treatment, with any elastase inhibitor or glucocorticoid) at the conclusion of the 12 week administration period.

One conclusion that can be drawn from FIGS. 6-8 is that elastase inhibition, through administration of an elastase inhibitor, a glucocorticoid or both, directly protects muscle fober stability and improves regeneration in dystrophic muscle.

Other conclusions that can be drawn from FIGS. 1-8 are (1) pharmacologic inhibition of neutrophil elastase in mice promotes muscle fiber stability and muscle regeneration; and (2) combination of elastase inhibition with a glucocorticoid enhances efficacy and decreases liver toxicity of the glucocorticoid.

Figure 9:
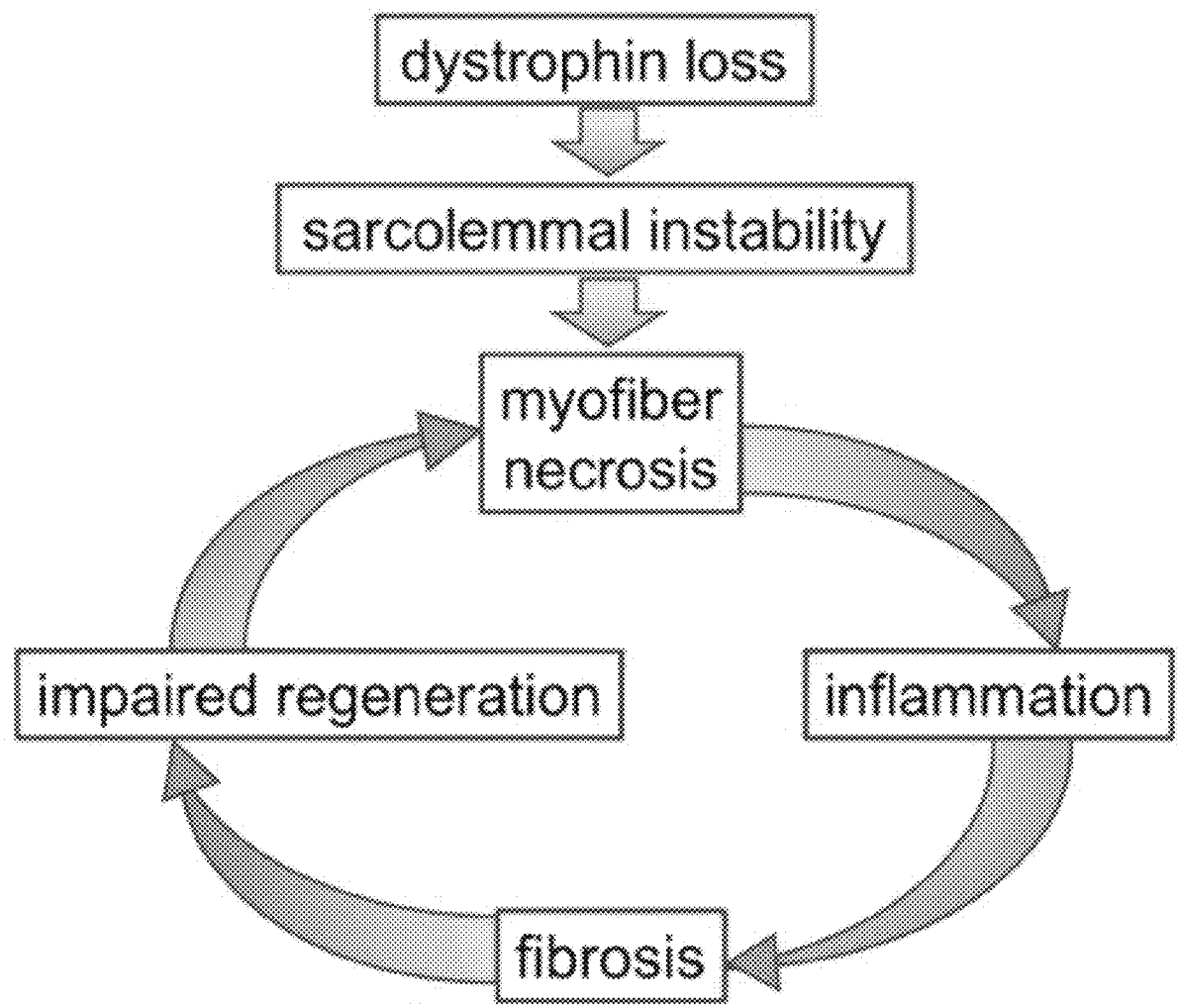
FIG. 9 is a diagram depicting a simplified summary of Duchenne muscular dystrophy (DMD) pathogenesis.

FIG. 9 is a diagram depicting a simplified summary of Duchenne muscular dystrophy (DMD) pathogenesis, which begins with myofiber fragility (due to dystrophin loss-induced sarcolemmal instability) and results in muscle loss or weakness. Various "boxes" of this summary are referred to in connection with other figures, as noted below.

Figure 10:
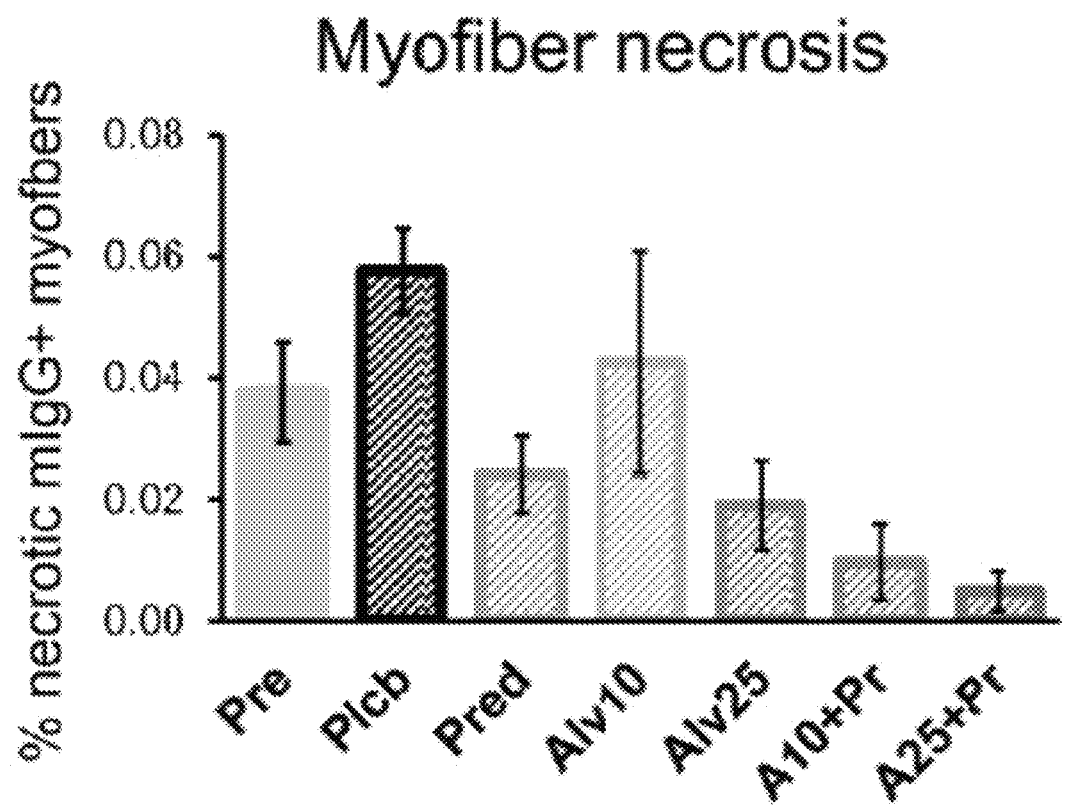
FIG. 10 is a graphical illustration of myofiber necrosis levels for various cohorts of tested mice.

A demonstration of the "myofiber necrosis" box of FIG. 9 is shown in FIG. 10, which is a graphical illustration of myofiber (a short for muscle fiber) necrosis values for various cohorts of the mice of FIGS. 1-8, at the conclusion of the 12 week administration period. In FIG. 10, myofiber necrosis was measured by calculating the percentage of myofibers that uptake mouse immunoglobulins (mIgG) on immunostained cryosections. IgG are normally present only in the blood and the extracellular matrix within tissues, but are uptaken by necrotic cells that have permeable plasma membranes due to cell damage damage. Thus, from FIG. 10, it can be concluded that the elastase inhibitor alvelestat decreases myofiber necrosis in a dose-dependent manner, and yields an additive affect on myofiber stability when combined with the glucocorticoid prednisolone.

Figure 11A:
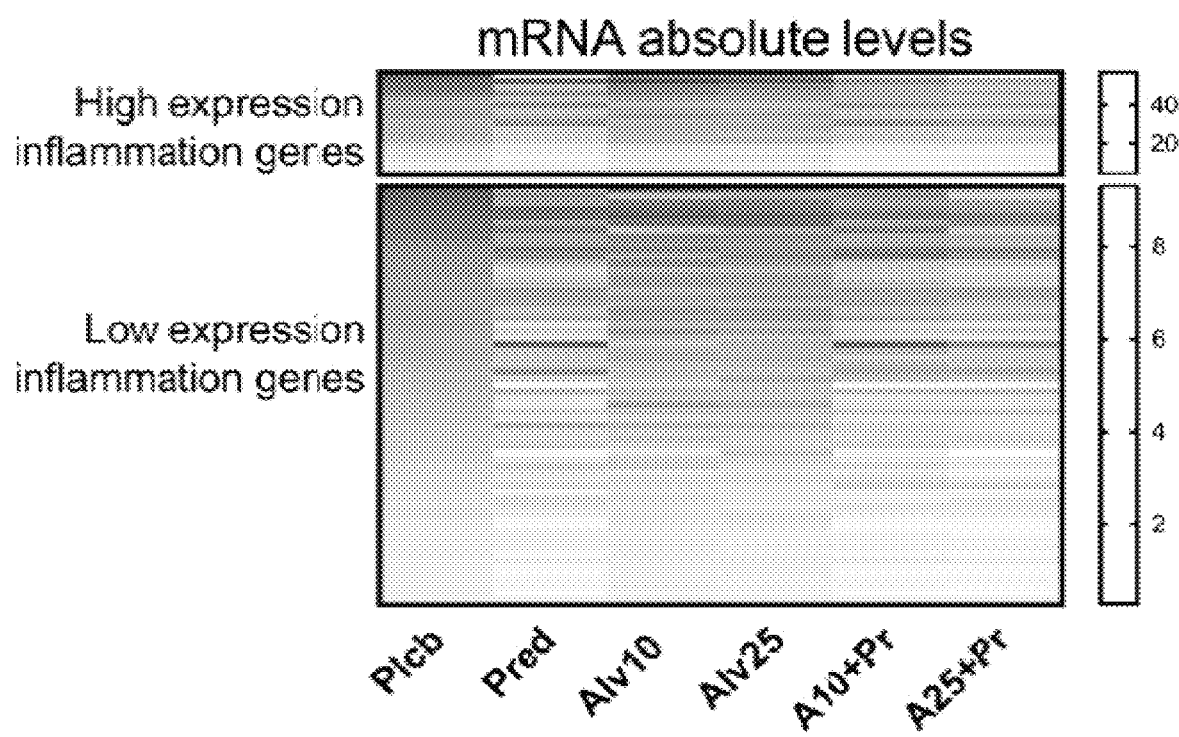
FIGS. 11A and 11B are illustrations of mRNA transcriptions for various cohorts of the mice.
Figure 11B:
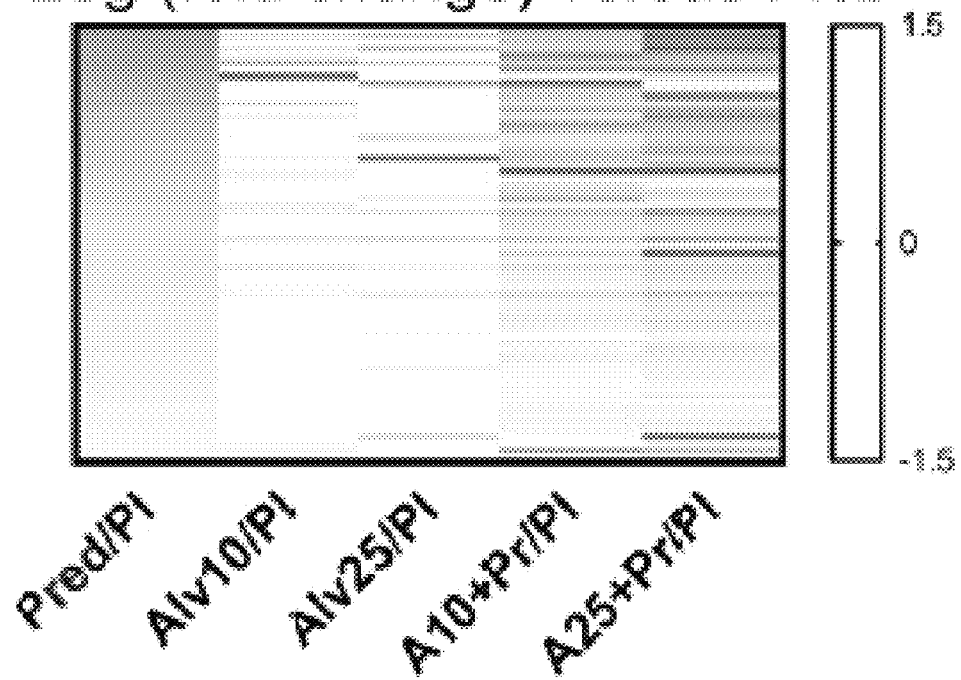

A demonstration of the "inflammation" box of FIG. 9 is shown in FIGS. 11A and 11B, which are illustrations of mRNA transcripts for various cohorts of the mice of FIGS. 1-8, at the conclusion of the 12 week administration period. In FIGS. 11A and 11B, mRNA was extracted from muscles of the mice, then transcripts were quantified using next generation sequencing. The absolute (normalized) transcript levels of genes involved in the immune response (cytokines, chemokines and their receptors) are shown in FIG. 11A, while FIG. 11B shows the Log(10) of the fold changes compared to placebo for inflammation-related transcripts that changed the most.

Further, in FIGS. 12A-12F, it is shown that elastase inhibition potentiates the immuno-suppressant activity of prednisolone. Mdx$^{4cv}$ mice were treated for 12 weeks with either placebo (Plcb, gray boxes) or prednisolone (1 mg/Kg/day, cyan boxes) alone or in combination with the elastase inhibitor alvelestat (Alv) at two different doses (10 mg/Kg/day, pink boxes; 25 mg/Kg/day, purple boxes). Each box-and-whiskers graph represent the levels of a marker of the immune response detected by RNA sequencing (n=6 per treatment group, Y-axis scale on the left). The overlayed line graphs show the effect size of each treatment vs Plcb calculated and plotted as Cohen's d (Y-axis scale on the right). Significance of each treatment vs Plcb: *=$p<0.001$, =$p<0.01$, *=$p<0.05$.

Further, as seen in FIGS. 11A and 11B that at the global level, neutrophil elastase (NE) inhibition does not appear to affect inflammation a significant amount, however, certain markers are affected by the addition of the elastase inhibitor to the glucocorticoid (FIGS. 12A-12F) which ultimately leads to a change in the "quality" of the immune response to injury, rather than the "quantity". Thus, from FIGS. 11A, 11B and 12A-12F it can be concluded that alvelestat does not significantly affect inflammation, either alone or in combination with prednisolone.

Figure 13:
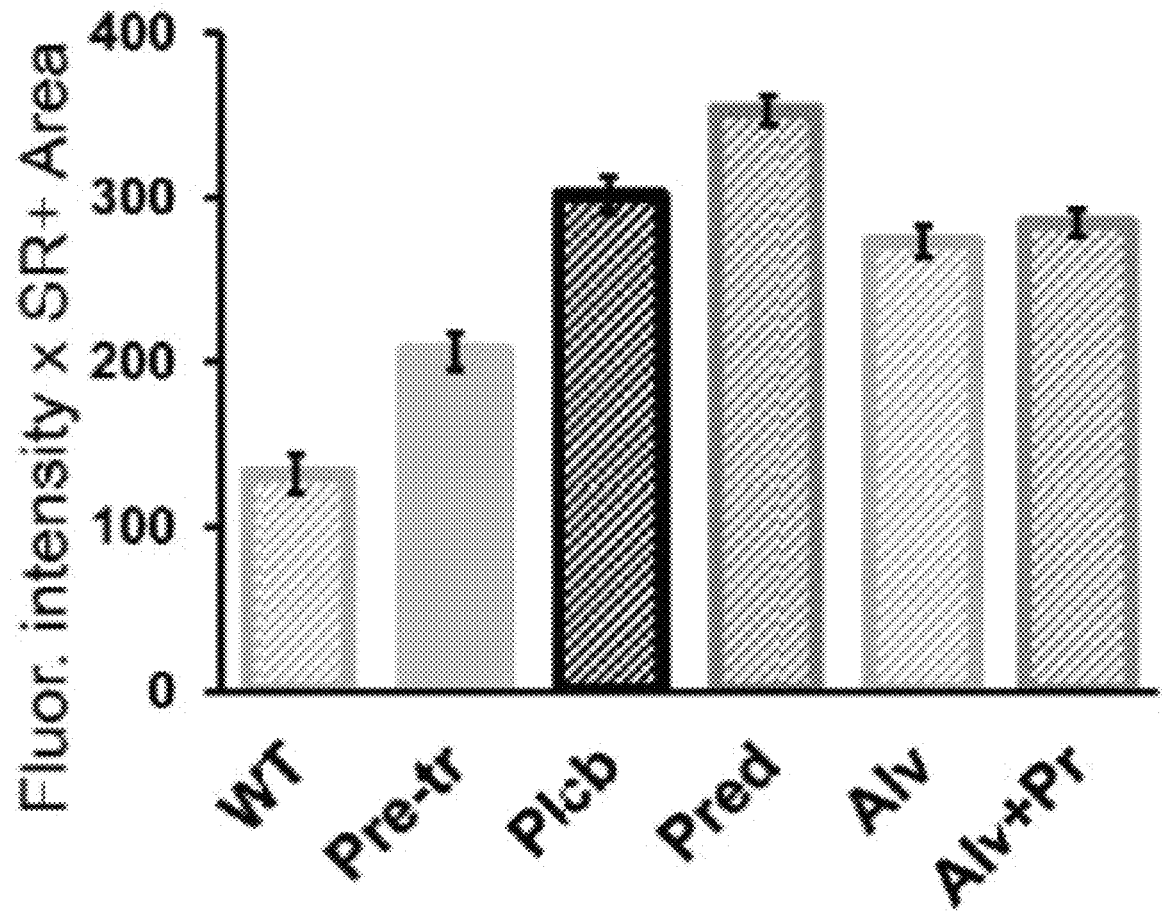
FIG. 13 is a graphical illustration of fibrosis levels for various cohorts of tested mice.

A demonstration of the "fibrosis" box of FIG. 9 is shown in FIG. 13, which is a graphical illustration of muscle fibrosis values for various cohorts of the mice of FIGS. 1-8, at the conclusion of the 12 week administration period. FIG. 13 illustrates fibrosis levels of the various cohorts, assessed on cryosections of gastrocnemius muscles from the mice, which were stained with Sirius Red to detect fibrillar collagen. Untreated dystrophic mice were euthanized at the age when treatments start (Pre-tr) and used as baseline for disease progression. Images were analyzed for their fluorescence intensity (Sirius red emits fluorescence in the yellow-red band of the light spectrum) as a measure of collagen abundance per unit area (e.g. per pixel), which was multiplied by the total Sirius red+ area as a proxy for 3D evaluation of fibrillar collagen content. Thus, from FIG. 13 it can be concluded that the elastase inhibitor alvelestat decreases muscle fibrosis and prevents prednisolone-induced fibrosis. FIG. 3 shows representative images of muscle cryosections stained with Sirius Red.

Figure 14:
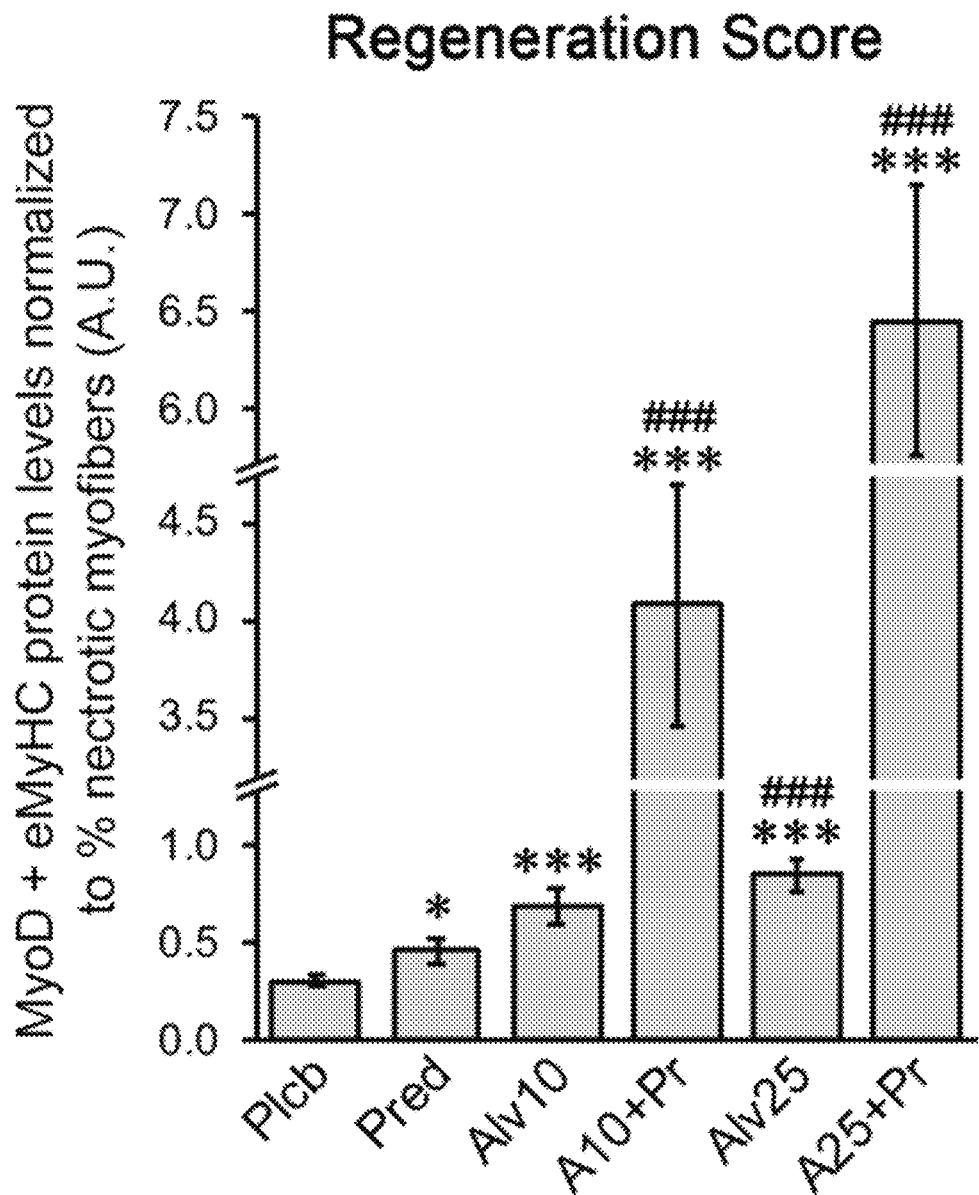
FIG. 14 is a graphical illustration of regeneration score levels for various cohorts of tested mice.

A demonstration of the "impaired regeneration" box of FIG. 9 is shown in FIG. 14, which is a graphical illustration of a regeneration score. For FIG. 14 both MyoD and embryonic myosin heavy chain (eMyHC) protein levels were measure by western blotting in quadriceps muscles of mdx$^{4cv}$ mice treated for 12 weeks as indicated. For each mouse, the raw value for both MyoD and eMyHC was normalized to the average of the Placebo (Plcb) group so that the values of MyoD and eMyHC could added to generate a cumulative value of regeneration markers, where the early marker MyoD weighed equally to the late marker eMyHC. Since regeneration is the response to injury-induced necrosis and since it is shown that elastase inhibition by alvelestat reduces necrosis (lowers serum mCK levels), the cumulative regeneration marker values for each mouse were normalized to average necrosis score (percentage of necrotic myofibers) for the same group to obtain a true Regeneration Score. This figure shows that: (a) elastase inhibition improves muscle regeneration in a dose-dependent manner and more effectively than a glucocorticoid alone; (b) addition of an elastase inhibitor to a glucocorticoid yields a synergistic enhancement of efficacy. Significance vs Plcb: *=p<0.05, ***=p<0.001; significance vs Pred: ####=p<0.001.

Figure 15:
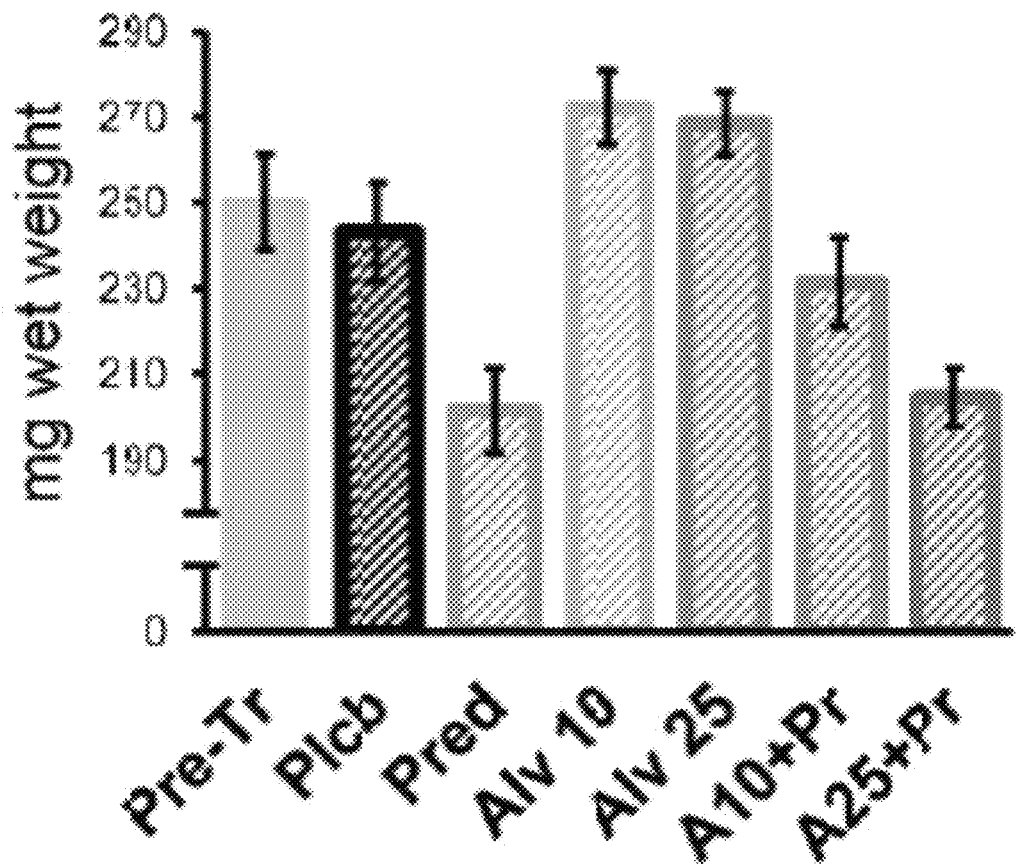
FIG. 15 is a graphical illustration of quadriceps weight levels for various cohorts of tested mice.
Figure 16:
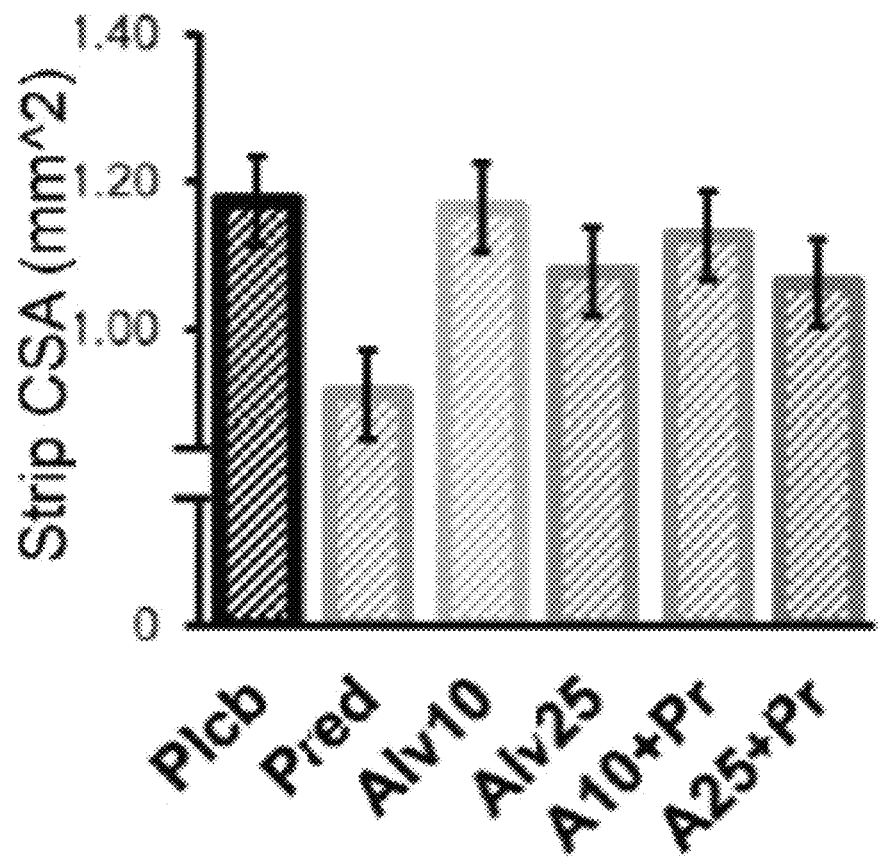
FIG. 16 is a graphical illustration of diaphragm cross section area (CSA) levels for various cohorts of tested mice.

A demonstration of the "muscle loss" box of FIG. 9 is shown in FIGS. 15 and 16, which are graphical illustrations of quadriceps weight and diaphragm cross sectional areas (CSA) for various cohorts of the mice of FIGS. 1-8, at the conclusion of the 12 week administration period. FIG. 15 illustrates the wet weight of quadriceps muscle groups dissected from dystrophic mice at treatment start (baseline, Pre-Tr) or after the 12 week administration period, at the time of euthanasia. While the glucocorticoid prednisolone dramatically decreased muscle mass, the elastase inhibitor alvelestat increased it and partly rescued the prednisolone-induced loss of muscle mass in a dose-dependent manner that appears inversely correlated. FIG. 16 illustrates the cross-sectional areas of muscle strips obtained from the lateral portion of the diaphragm, which follow a similar trend to quadriceps wet weights. Thus, what can be concluded from FIGS. 15 and 16 is that alvelestat promotes muscle growth and/or prevents prednisolone-induced muscle loss.

Figure 17:
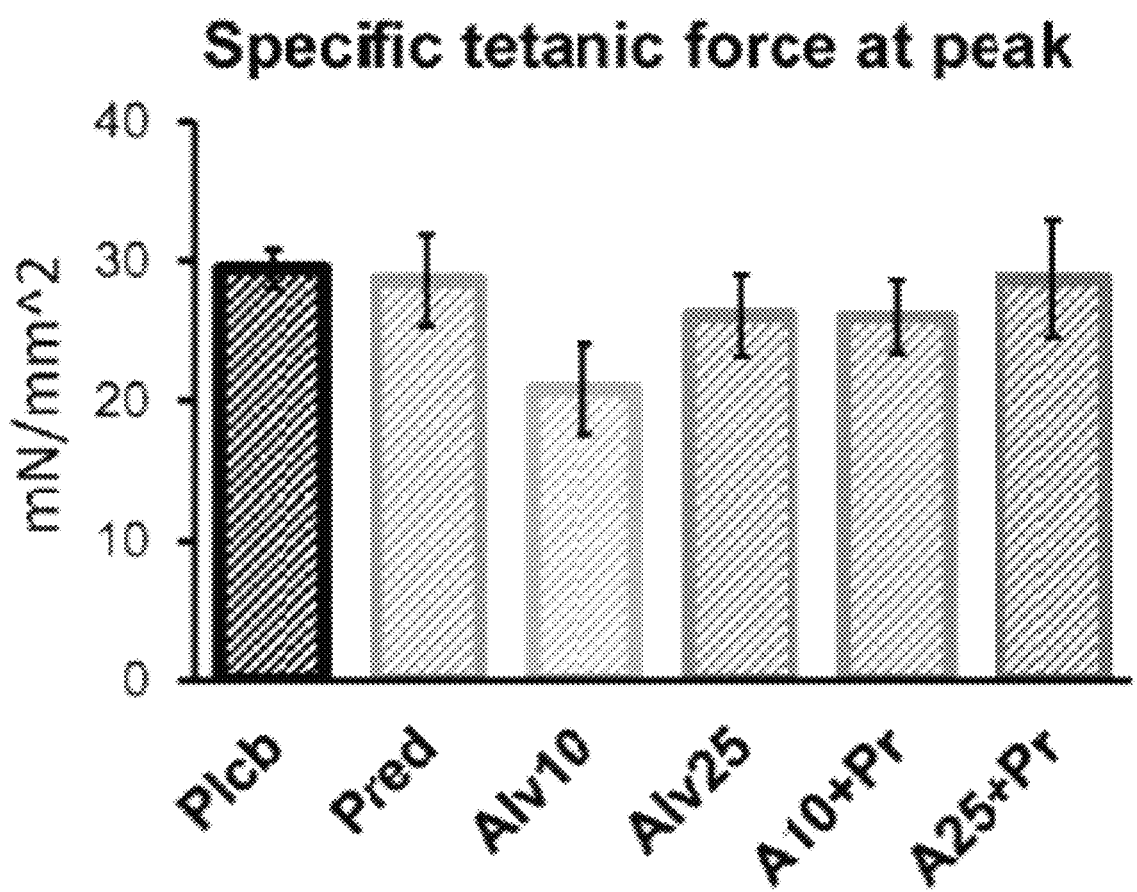
FIG. 17 is a graphical illustration of tetanic force levels for various cohorts of tested mice.

A demonstration of the "Muscle Weakness" box of FIG. 9 is shown in FIG. 17, which is a graphical illustration of titanic force values for various cohorts of the mice of FIGS. 1-8, at the conclusion of the 12 week administration period. For FIG. 17, diaphragm strips were clamped to a force transducer via the central tendon and the rib was immersed in a continually oxygenated Ringer's buffer, and maintained at 37° C. The specific tetanic force was calculated as the ratio between the peak titanic force (=maximum force elicited in response to a tetanic stimulus) and the cross-sectional area of the diaphragm strip.

Figure 18:
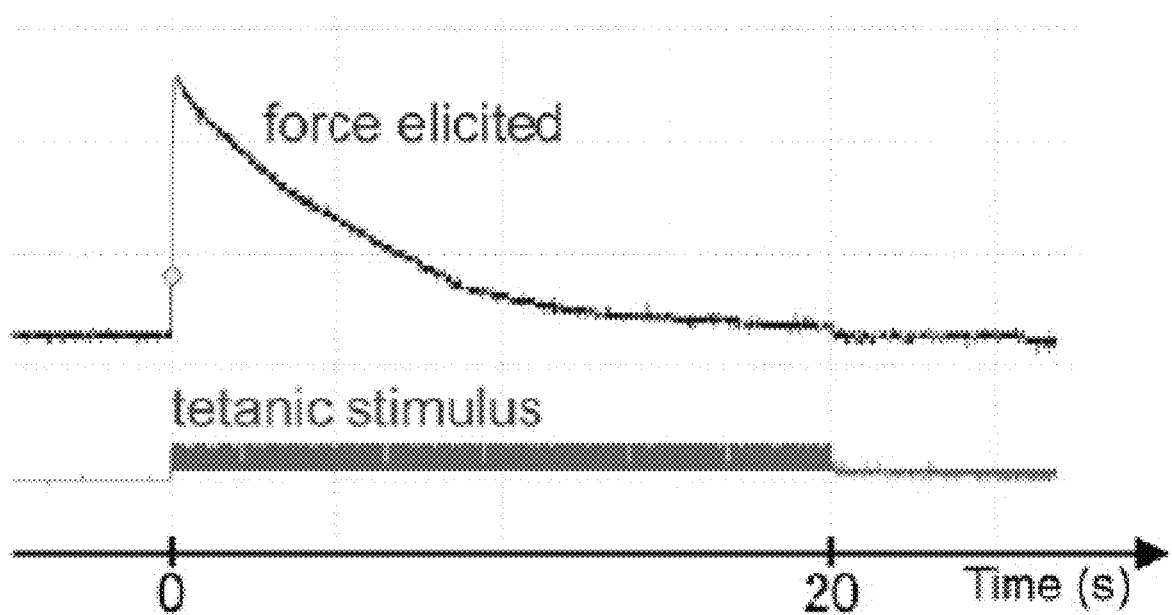
FIG. 18 is a graphical illustration of a protocol use for tetanic stimulation of diaphragm strips and a typical force trace recorded in response.

FIG. 18 is an illustration of a representative force trace obtained by stimulating diaphragm strips with a 20 second long tetanus. The maximum (peak) force is achieved shortly after beginning of the tetanic stimulation, then the force declines as a combination of muscle fatigue and contraction-induced damage occurs.

Figure 19:
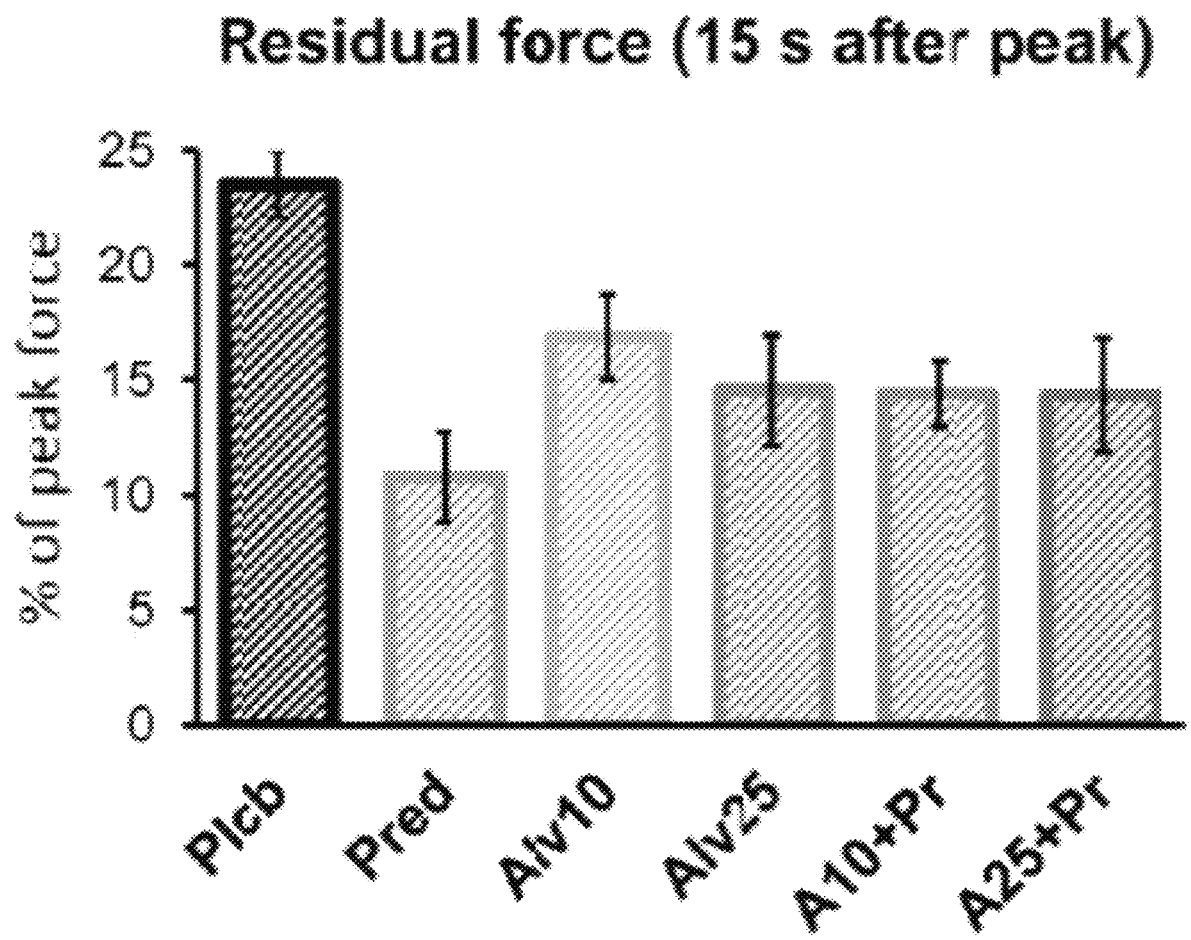
FIG. 19 is a graphical illustration of residual force levels after 5 minutes of tetanic stimulation for various cohorts of tested mice.

FIG. 19 is a graphical illustration of the residual force at 15 seconds after peak force is achieved (measured as percentage of the peak force), which is an estimate of the extent of contraction-induced damage and fatigue. Since all treatments reduce muscle damage as measured by serum mCK activity and myofiber necrosis (FIG. 10), then it was deduced that the treatment-induced decline in residual force, which is greater for prednisolone alone, is mainly caused by muscle fiber fatigue.

Thus, what can be concluded from FIGS. 17-19 is that the elastase inhibitor alvelestat, alone and in combination with prednisolone, affects diaphragm weakness independent of muscle loss in a complex manner.

The described embodiments and examples of the present disclosure are intended to be illustrative rather than restrictive, and are not intended to represent every embodiment or example of the present disclosure. While the fundamental novel features of the disclosure as applied to various specific embodiments thereof have been shown, described and pointed out, it will also be understood that various omissions, substitutions and changes in the form and details of the devices illustrated and in their operation, may be made by those skilled in the art without departing from the spirit of the disclosure. For example, it is expressly intended that all combinations of those elements and/or method steps which perform substantially the same function in substantially the same way to achieve the same results are within the scope of the disclosure. Moreover, it should be recognized that structures and/or elements and/or method steps shown and/or described in connection with any disclosed form or embodiment of the disclosure may be incorporated in any other disclosed or described or suggested form or embodiment as a general matter of design choice. Further, various modifications and variations can be made without departing from the spirit or scope of the disclosure as set forth in the following claims both literally and in equivalents recognized in law.

What is claimed is:

1. A method for promoting muscle regeneration in a subject with a myopathy comprising administering to the subject in need thereof a synergistically effective amount of an elastase inhibitor in combination with a glucocorticoid, wherein the elastase inhibitor is alvelestat and the glucocorticoid is prednisolone.

2. The method according to claim 1, wherein the elastase inhibitor is for promoting muscle regeneration by protecting muscle progenitor cells and muscle fiber stability.

3. The method according to claim 1, wherein the elastase inhibitor is provided in an amount sufficient to protect the regenerative potential of muscle progenitor cells and stability of muscle fibers.

4. The method according to claim 1, wherein the elastase inhibitor is a neutrophil elastase inhibitor.

5. The method according to claim 1, wherein the promotion of muscle regeneration and muscle fiber stability is for treatment of a myopathy associated with muscle inflammation.

6. The method according to claim 5, wherein the myopathy is selected from the group consisting of: muscular dystrophy, dermatomyositis, inclusion body myositis, congenital inflammatory myopathy, polymyositis, chronic obstructive pulmonary disease (COPD) induced myopathy and/or atrophy, infection-induced myopathy and/or atrophy, cancer-induced myopathy and/or cachexia, immobility-induced atrophy and sarcopenia.

7. The method according to claim 6, wherein the muscular dystrophy is Duchenne Muscular Dystrophy.

8. The method according to claim 1, wherein mCK activity is decreased relative to glucocorticoid treatment alone.

9. The method according to claim 1, wherein TGF-β levels are decreased relative to glucocorticoid treatment alone.

10. The method according to claim 1, wherein muscle fibrosis is decreased relative to glucocorticoid treatment alone.

11. The method according to claim 1, wherein the levels of MyoD are decreased relative to glucocorticoid treatment alone.

12. The method according to claim 1, wherein the elastase inhibitor is provided in an amount sufficient to decrease mCK activity relative to glucorticoid treatment alone.

13. The method according to claim 1, wherein promoting muscle regeneration further prevents glucocorticoid induced muscle wasting.

* * * * *